US012721668B2

(12) United States Patent
Pham et al.

(10) Patent No.: US 12,721,668 B2
(45) Date of Patent: Sep. 1, 2026

(54) MEDICAL DEVICE WITH AN END EFFECTOR INCLUDING CONNECTING HUBS AND AN ELECTRODE ARRAY

(71) Applicant: Biosense Webster (Israel) Ltd., Yokneam (IL)

(72) Inventors: Cuong Pham, Westminster, CA (US); Helee Mukul Joshi, Mission Viejo, CA (US); Thanh Nguyen, El Monte, CA (US); Keshava Datta, Chino Hills, CA (US); Isabel Barbero Solte, Orange, CA (US)

(73) Assignee: Biosense Webster (Israel) Ltd., Yokneam (IL)

(*) Notice: Subject to any disclaimer, the term of this patent is extended or adjusted under 35 U.S.C. 154(b) by 289 days.

(21) Appl. No.: 18/473,106

(22) Filed: Sep. 22, 2023

(65) Prior Publication Data

US 2025/0099160 A1 Mar. 27, 2025

(51) Int. Cl.
*A61B 18/14* (2006.01)
*A61B 18/00* (2006.01)

(52) U.S. Cl.
CPC .... *A61B 18/14* (2013.01); *A61B 2018/00172* (2013.01); *A61B 2018/00267* (2013.01); *A61B 2018/00613* (2013.01); *A61B 2018/1467* (2013.01); *A61B 2018/1475* (2013.01); *A61B 2218/002* (2013.01)

(58) Field of Classification Search
CPC ........... A61B 2018/00172; A61B 2018/00267; A61B 2018/0016; A61B 2018/00357; A61B 2018/00613; A61B 2018/1467; A61B 2018/1475; A61B 2018/00577; A61B 5/6858; A61B 5/6859; A61B 5/287; A61B 18/14; A61B 18/1492; A61B 17/221
See application file for complete search history.

(56) References Cited

U.S. PATENT DOCUMENTS 4,699,147 A 10/1987 Chilson et al.
4,940,064 A 7/1990 Desai
5,215,103 A 6/1993 Desai
5,255,679 A 10/1993 Imran
(Continued)

FOREIGN PATENT DOCUMENTS

CN 111248993 A 6/2020
CN 111248996 A 6/2020
(Continued)

OTHER PUBLICATIONS

Extended European Search Report and Opinion dated Jan. 21, 2025, from corresponding European Application No. 24201608.7.

*Primary Examiner* — Joseph A Stoklosa
*Assistant Examiner* — Marina Delaney Templeton

(57) ABSTRACT

The disclosed technology includes a connecting hub used with an end effector of a medical probe. The connecting hub is generally cylindrical in form and defines a hub lumen extending along a longitudinal axis between its terminal ends. Recesses are disposed about an outer circumferential surface of the cylindrical body and extend parallel to the longitudinal axis. Each recess is open along the longitudinal axis at or proximal the first terminal end and mates with a proximal end or a distal end of a spine of the end effector.

13 Claims, 13 Drawing Sheets

(56) References Cited

U.S. PATENT DOCUMENTS 5,293,869 A 3/1994 Edwards et al.
5,309,910 A 5/1994 Edwards et al.
5,313,943 A 5/1994 Houser et al.
5,324,284 A 6/1994 Imran
5,345,936 A 9/1994 Pomeranz et al.
5,365,926 A 11/1994 Desai
5,391,199 A 2/1995 Ben-Haim
5,396,887 A 3/1995 Imran
5,400,783 A 3/1995 Pomeranz et al.
5,411,025 A 5/1995 Webster, Jr.
5,415,166 A 5/1995 Imran
5,443,489 A 8/1995 Ben-Haim
5,456,254 A 10/1995 Pietroski et al.
5,465,717 A 11/1995 Imran et al.
5,476,495 A 12/1995 Kordis et al.
5,499,981 A 3/1996 Kordis
5,526,810 A 6/1996 Wang
5,546,940 A 8/1996 Panescu et al.
5,549,108 A 8/1996 Edwards et al.
5,558,073 A 9/1996 Pomeranz et al.
5,558,091 A 9/1996 Acker et al.
5,577,509 A 11/1996 Panescu et al.
5,595,183 A 1/1997 Swanson et al.
5,598,848 A 2/1997 Swanson et al.
5,609,157 A 3/1997 Panescu et al.
5,628,313 A 5/1997 Webster, Jr.
5,681,280 A 10/1997 Rusk et al.
5,722,401 A 3/1998 Pietroski et al.
5,722,403 A 3/1998 McGee et al.
5,725,525 A 3/1998 Kordis
5,730,128 A 3/1998 Pomeranz et al.
5,772,590 A 6/1998 Webster, Jr.
5,782,899 A 7/1998 Imran
5,823,189 A 10/1998 Kordis
5,881,727 A 3/1999 Edwards
5,893,847 A 4/1999 Kordis
5,904,680 A 5/1999 Kordis et al.
5,911,739 A 6/1999 Kordis et al.
5,928,228 A 7/1999 Kordis et al.
5,968,040 A 10/1999 Swanson et al.
6,014,579 A 1/2000 Pomeranz et al.
6,014,590 A 1/2000 Whayne et al.
6,119,030 A 9/2000 Morency
6,142,993 A 11/2000 Whayne et al.
6,172,499 B1 1/2001 Ashe
6,216,043 B1 4/2001 Swanson et al.
6,216,044 B1 4/2001 Kordis
6,239,724 B1 5/2001 Doron et al.
6,332,089 B1 12/2001 Acker et al.
6,428,537 B1 8/2002 Swanson et al.
6,456,864 B1 9/2002 Swanson et al.
6,484,118 B1 11/2002 Govari
6,574,492 B1 6/2003 Ben-Haim et al.
6,584,345 B2 6/2003 Govari
6,600,948 B2 7/2003 Ben-Haim et al.
6,618,612 B1 9/2003 Acker et al.
6,690,963 B2 2/2004 Ben-Haim et al.
6,738,655 B1 5/2004 Sen et al.
6,741,878 B2 5/2004 Fuimaono et al.
6,748,255 B2 6/2004 Fuimaono et al.
6,780,183 B2 8/2004 Jimenez, Jr. et al.
6,788,967 B2 9/2004 Ben-Haim et al.
6,837,886 B2 1/2005 Collins et al.
6,866,662 B2 3/2005 Fuimaono et al.
6,892,091 B1 5/2005 Ben-Haim et al.
6,970,730 B2 11/2005 Fuimaono et al.
6,973,340 B2 12/2005 Fuimaono et al.
6,980,858 B2 12/2005 Fuimaono et al.
7,048,734 B1 5/2006 Fleischman et al.
7,149,563 B2 12/2006 Fuimaono et al.
7,255,695 B2 8/2007 Falwell et al.
7,257,434 B2 8/2007 Fuimaono et al.
7,399,299 B2 7/2008 Daniel et al.
7,410,486 B2 8/2008 Fuimaono et al.
7,522,950 B2 4/2009 Fuimaono et al.
7,536,218 B2 5/2009 Govari et al.
RE41,334 E 5/2010 Beatty et al.
7,756,576 B2 7/2010 Levin
7,846,157 B2 12/2010 Kozel
7,848,787 B2 12/2010 Osadchy
7,869,865 B2 1/2011 Govari et al.
7,930,018 B2 4/2011 Harlev et al.
8,007,495 B2 8/2011 McDaniel et al.
8,048,063 B2 11/2011 Aeby et al.
8,103,327 B2 1/2012 Harlev et al.
8,167,845 B2 5/2012 Wang et al.
8,224,416 B2 7/2012 De La Rama et al.
8,235,988 B2 8/2012 Davis et al.
8,346,339 B2 1/2013 Kordis et al.
8,435,232 B2 5/2013 Aeby et al.
8,447,377 B2 5/2013 Harlev et al.
8,456,182 B2 6/2013 Bar-Tal et al.
8,498,686 B2 7/2013 Grunewald
8,517,999 B2 8/2013 Pappone et al.
8,545,490 B2 10/2013 Mihajlovic et al.
8,560,086 B2 10/2013 Just et al.
8,567,265 B2 10/2013 Aeby et al.
8,712,550 B2 4/2014 Grunewald
8,755,861 B2 6/2014 Harlev et al.
8,825,130 B2 9/2014 Just et al.
8,906,011 B2 12/2014 Gelbart et al.
8,945,120 B2 2/2015 McDaniel et al.
8,979,839 B2 3/2015 De La Rama et al.
9,037,264 B2 5/2015 Just et al.
9,131,980 B2 9/2015 Bloom
9,204,929 B2 12/2015 Solis
9,277,960 B2 3/2016 Weinkam et al.
9,314,208 B1 4/2016 Altmann et al.
9,339,331 B2 5/2016 Tegg et al.
9,486,282 B2 11/2016 Solis
9,554,718 B2 1/2017 Bar-Tal et al.
D782,686 S 3/2017 Werneth et al.
9,585,588 B2 3/2017 Marecki et al.
9,597,036 B2 3/2017 Aeby et al.
9,687,297 B2 6/2017 Just et al.
9,693,733 B2 7/2017 Altmann et al.
9,782,099 B2 10/2017 Williams et al.
9,788,895 B2 10/2017 Solis
9,801,681 B2 10/2017 Laske et al.
9,814,618 B2 11/2017 Nguyen et al.
9,833,161 B2 12/2017 Govari
9,894,756 B2 2/2018 Weinkam et al.
9,895,073 B2 2/2018 Solis
9,907,609 B2 3/2018 Cao et al.
9,974,460 B2 5/2018 Wu et al.
9,986,949 B2 6/2018 Govari et al.
9,993,160 B2 6/2018 Salvestro et al.
10,014,607 B1 7/2018 Govari et al.
10,028,376 B2 7/2018 Weinkam et al.
10,034,637 B2 7/2018 Harlev et al.
10,039,494 B2 8/2018 Altmann et al.
10,045,707 B2 8/2018 Govari
10,078,713 B2 9/2018 Auerbach et al.
10,111,623 B2 10/2018 Jung et al.
10,130,420 B2 11/2018 Basu et al.
10,136,828 B2 11/2018 Houben et al.
10,143,394 B2 12/2018 Solis
10,172,536 B2 1/2019 Maskara et al.
10,182,762 B2 1/2019 Just et al.
10,194,818 B2 2/2019 Williams et al.
10,201,311 B2 2/2019 Chou et al.
10,219,860 B2 3/2019 Harlev et al.
10,219,861 B2 3/2019 Just et al.
10,231,328 B2 3/2019 Weinkam et al.
10,238,309 B2 3/2019 Bar-Tal et al.
10,278,590 B2 5/2019 Salvestro et al.
D851,774 S 6/2019 Werneth et al.
10,314,505 B2 6/2019 Williams et al.
10,314,507 B2 6/2019 Govari et al.
10,314,648 B2 6/2019 Ge et al.
10,314,649 B2 6/2019 Bakos et al.
10,349,855 B2 7/2019 Zeidan et al.
10,350,003 B2 7/2019 Weinkam et al.
10,362,991 B2 7/2019 Tran et al.

(56) References Cited

U.S. PATENT DOCUMENTS 10,375,827 B2 8/2019 Weinkam et al.
10,376,170 B2 8/2019 Quinn et al.
10,376,221 B2 8/2019 Iyun et al.
10,398,348 B2 9/2019 Osadchy et al.
10,403,053 B2 9/2019 Katz et al.
10,441,188 B2 10/2019 Katz et al.
10,470,682 B2 11/2019 Deno et al.
10,470,714 B2 11/2019 Altmann et al.
10,482,198 B2 11/2019 Auerbach et al.
10,492,857 B2 12/2019 Guggenberger et al.
10,542,620 B2 1/2020 Weinkam et al.
10,575,743 B2 3/2020 Basu et al.
10,575,745 B2 3/2020 Solis
10,582,871 B2 3/2020 Williams et al.
10,582,894 B2 3/2020 Ben Zrihem et al.
10,596,346 B2 3/2020 Aeby et al.
10,602,947 B2 3/2020 Govari et al.
10,617,867 B2 4/2020 Viswanathan et al.
10,660,702 B2 5/2020 Viswanathan et al.
10,667,753 B2 6/2020 Werneth et al.
10,674,929 B2 6/2020 Houben et al.
10,681,805 B2 6/2020 Weinkam et al.
10,682,181 B2 6/2020 Cohen et al.
10,687,892 B2 6/2020 Long et al.
10,702,178 B2 7/2020 Dahlen et al.
10,716,477 B2 7/2020 Salvestro et al.
10,758,304 B2 9/2020 Aujla
10,765,371 B2 9/2020 Hayam et al.
10,772,566 B2 9/2020 Aujila
10,799,281 B2 10/2020 Goertzen et al.
10,842,558 B2 11/2020 Harlev et al.
10,842,561 B2 11/2020 Viswanathan et al.
10,863,914 B2 12/2020 Govari et al.
10,881,376 B2 1/2021 Shemesh et al.
10,898,139 B2 1/2021 Guta et al.
10,905,329 B2 2/2021 Bar-Tal et al.
10,912,484 B2 2/2021 Ziv-Ari et al.
10,918,306 B2 2/2021 Govari et al.
10,939,871 B2 3/2021 Altmann et al.
10,952,795 B2 3/2021 Cohen et al.
10,973,426 B2 4/2021 Williams et al.
10,973,461 B2 4/2021 Baram et al.
10,987,045 B2 4/2021 Basu et al.
11,006,902 B1 5/2021 Bonyak et al.
11,040,208 B1 6/2021 Govari et al.
11,045,628 B2 6/2021 Beeckler et al.
11,051,877 B2 7/2021 Sliwa et al.
11,109,788 B2 9/2021 Rottmann et al.
11,116,435 B2 9/2021 Urman et al.
11,129,574 B2 9/2021 Cohen et al.
11,160,482 B2 11/2021 Solis
11,164,371 B2 11/2021 Yellin et al.
2002/0198522 A1 12/2002 Kordis
2004/0210121 A1 10/2004 Fuimaono et al.
2006/0009689 A1 1/2006 Fuimaono et al.
2006/0009690 A1 1/2006 Fuimaono et al.
2006/0100669 A1 5/2006 Fuimaono et al.
2007/0093806 A1 4/2007 Desai et al.
2007/0161966 A1 7/2007 West et al.
2007/0276212 A1 11/2007 Fuimaono et al.
2008/0234564 A1 9/2008 Beatty et al.
2010/0168647 A1* 7/2010 Tegg .................. A61B 18/1492 604/21
2011/0118726 A1 5/2011 De La Rama et al.
2011/0160574 A1 6/2011 Harlev et al.
2011/0190625 A1 8/2011 Harlev et al.
2011/0245756 A1 10/2011 Arora et al.
2011/0301597 A1 12/2011 McDaniel et al.
2013/0090651 A1 4/2013 Smith
2013/0116688 A1 5/2013 Kunis et al.
2013/0172715 A1* 7/2013 Just ...................... A61B 5/6858 606/41
2013/0172872 A1 7/2013 Subramaniam et al.
2013/0172883 A1 7/2013 Lopes et al.
2013/0178850 A1 7/2013 Lopes et al.
2013/0190587 A1 7/2013 Lopes et al.
2013/0296852 A1 11/2013 Madjarov et al.
2014/0018788 A1 1/2014 Engelman et al.
2014/0025069 A1 1/2014 Willard et al.
2014/0052118 A1 2/2014 Laske et al.
2014/0180147 A1 6/2014 Thakur et al.
2014/0180151 A1 6/2014 Maskara et al.
2014/0180152 A1 6/2014 Maskara et al.
2014/0257069 A1 9/2014 Eliason et al.
2014/0276712 A1 9/2014 Mallin et al.
2014/0276788 A1 9/2014 Nguyen et al.
2014/0309512 A1 10/2014 Govari et al.
2015/0011991 A1 1/2015 Buysman et al.
2015/0045863 A1* 2/2015 Litscher ............. A61B 18/1492 607/116
2015/0080693 A1 3/2015 Solis
2015/0105770 A1 4/2015 Amit
2015/0119878 A1 4/2015 Heisel et al.
2015/0133919 A1 5/2015 McDaniel et al.
2015/0208942 A1 7/2015 Bar-Tal et al.
2015/0250424 A1 9/2015 Govari et al.
2015/0270634 A1 9/2015 Buesseler et al.
2015/0342491 A1 12/2015 Marecki et al.
2015/0342532 A1 12/2015 Basu et al.
2016/0081746 A1 3/2016 Solis
2016/0113582 A1 4/2016 Altmann et al.
2016/0113709 A1 4/2016 Maor
2016/0183877 A1 6/2016 Williams et al.
2016/0228023 A1 8/2016 Govari
2016/0228062 A1 8/2016 Altmann et al.
2016/0278853 A1 9/2016 Ogle et al.
2016/0302858 A1 10/2016 Bencini
2016/0338770 A1 11/2016 Bar-Tal et al.
2017/0027638 A1 2/2017 Solis
2017/0065227 A1* 3/2017 Marrs .................. A61B 5/6858
2017/0071543 A1 3/2017 Basu et al.
2017/0071544 A1 3/2017 Basu et al.
2017/0071665 A1 3/2017 Solis
2017/0095173 A1 4/2017 Bar-Tal et al.
2017/0100187 A1 4/2017 Basu et al.
2017/0143227 A1 5/2017 Marecki et al.
2017/0156790 A1 6/2017 Aujla
2017/0172442 A1 6/2017 Govari
2017/0185702 A1 6/2017 Auerbach et al.
2017/0202515 A1 7/2017 Zrihem et al.
2017/0221262 A1 8/2017 Laughner et al.
2017/0224958 A1 8/2017 Cummings et al.
2017/0265812 A1 9/2017 Williams et al.
2017/0281031 A1 10/2017 Houben et al.
2017/0281268 A1* 10/2017 Tran ................... A61B 18/1492
2017/0296125 A1 10/2017 Altmann et al.
2017/0296251 A1 10/2017 Wu et al.
2017/0319269 A1 11/2017 Oliverius et al.
2017/0347959 A1 12/2017 Guta et al.
2017/0354338 A1 12/2017 Levin et al.
2017/0354339 A1 12/2017 Zeidan et al.
2017/0354364 A1 12/2017 Bar-Tal et al.
2018/0008203 A1 1/2018 Iyun et al.
2018/0028084 A1 2/2018 Williams et al.
2018/0049803 A1 2/2018 Solis
2018/0085064 A1 3/2018 Auerbach et al.
2018/0132749 A1 5/2018 Govari et al.
2018/0137687 A1 5/2018 Katz et al.
2018/0160936 A1 6/2018 Govari et al.
2018/0160978 A1 6/2018 Cohen et al.
2018/0168511 A1 6/2018 Hall et al.
2018/0184982 A1 7/2018 Basu et al.
2018/0192958 A1 7/2018 Wu
2018/0206792 A1 7/2018 Auerbach et al.
2018/0235692 A1 8/2018 Efimov et al.
2018/0249959 A1 9/2018 Osypka
2018/0256109 A1 9/2018 Wu et al.
2018/0279954 A1 10/2018 Hayam et al.
2018/0303414 A1 10/2018 Toth et al.
2018/0310987 A1 11/2018 Altmann et al.
2018/0311497 A1 11/2018 Viswanathan et al.
2018/0338722 A1 11/2018 Altmann et al.
2018/0344188 A1 12/2018 Govari
2018/0344202 A1 12/2018 Bar-Tal et al.

(56) References Cited

U.S. PATENT DOCUMENTS

2018/0344251 A1 12/2018 Harlev et al.
2018/0344393 A1 12/2018 Gruba et al.
2018/0360534 A1 12/2018 Teplitsky et al.
2018/0365355 A1 12/2018 Auerbach et al.
2019/0000540 A1 1/2019 Cohen et al.
2019/0008582 A1 1/2019 Govari et al.
2019/0015007 A1 1/2019 Rottmann et al.
2019/0030328 A1 1/2019 Stewart et al.
2019/0049433 A1* 2/2019 Ehret .................... A61B 5/273
2019/0053708 A1 2/2019 Gliner
2019/0059766 A1 2/2019 Houben et al.
2019/0069949 A1 3/2019 Vrba et al.
2019/0069950 A1 3/2019 Viswanathan et al.
2019/0069954 A1 3/2019 Cohen et al.
2019/0117111 A1 4/2019 Osadchy et al.
2019/0117303 A1 4/2019 Claude et al.
2019/0117315 A1 4/2019 Keyes et al.
2019/0125439 A1 5/2019 Rohl et al.
2019/0133552 A1 5/2019 Shemesh et al.
2019/0142293 A1 5/2019 Solis
2019/0164633 A1 5/2019 Ingel et al.
2019/0167137 A1 6/2019 Bar-Tal et al.
2019/0167140 A1 6/2019 Williams et al.
2019/0188909 A1 6/2019 Yellin et al.
2019/0201664 A1 7/2019 Govari
2019/0209089 A1 7/2019 Baram et al.
2019/0216346 A1 7/2019 Ghodrati et al.
2019/0216347 A1 7/2019 Ghodrati et al.
2019/0231421 A1 8/2019 Mswanathan et al.
2019/0231423 A1 8/2019 Weinkam et al.
2019/0239811 A1 8/2019 Just et al.
2019/0246935 A1 8/2019 Govari et al.
2019/0298442 A1 10/2019 Ogata et al.
2019/0314083 A1 10/2019 Herrera et al.
2019/0328260 A1 10/2019 Zeidan et al.
2019/0343580 A1 11/2019 Nguyen et al.
2020/0000518 A1 1/2020 Kiernan et al.
2020/0008705 A1 1/2020 Ziv-Ari et al.
2020/0008869 A1 1/2020 Byrd
2020/0009378 A1 1/2020 Stewart et al.
2020/0015890 A1 1/2020 To et al.
2020/0022653 A1 1/2020 Moisa
2020/0029845 A1 1/2020 Baram et al.
2020/0046421 A1 2/2020 Govari
2020/0046423 A1 2/2020 Mswanathan et al.
2020/0060569 A1 2/2020 Tegg
2020/0077959 A1 3/2020 Altmann et al.
2020/0093539 A1 3/2020 Long et al.
2020/0129089 A1 4/2020 Gliner et al.
2020/0129125 A1 4/2020 Govari et al.
2020/0129128 A1 4/2020 Gliner et al.
2020/0155194 A1 5/2020 Schneider et al.
2020/0163707 A1 5/2020 Sliwa et al.
2020/0179650 A1 6/2020 Beeckler et al.
2020/0196896 A1 6/2020 Solis
2020/0205689 A1 7/2020 Squires et al.
2020/0205690 A1 7/2020 Williams et al.
2020/0205737 A1 7/2020 Beeckler
2020/0205876 A1 7/2020 Govari
2020/0205892 A1 7/2020 Viswanathan et al.
2020/0206461 A1 7/2020 Govari et al.
2020/0206498 A1 7/2020 Arora et al.
2020/0289197 A1 9/2020 Viswanathan et al.
2020/0297234 A1 9/2020 Houben et al.
2020/0297281 A1 9/2020 Basu et al.
2020/0305726 A1 10/2020 Salvestro et al.
2020/0305946 A1 10/2020 DeSimone et al.
2020/0375657 A1 12/2020 Olson et al.
2020/0397328 A1 12/2020 Altmann et al.
2020/0398048 A1 12/2020 Krimsky et al.
2021/0015549 A1 1/2021 Haghighi-Mood et al.
2021/0022684 A1 1/2021 Govari et al.
2021/0045805 A1 2/2021 Govari et al.
2021/0059549 A1 3/2021 Urman et al.
2021/0059550 A1 3/2021 Urman et al.
2021/0059608 A1 3/2021 Beeckler et al.
2021/0059743 A1 3/2021 Govari
2021/0059747 A1 3/2021 Krans et al.
2021/0077184 A1 3/2021 Basu et al.
2021/0082157 A1 3/2021 Rosenberg et al.
2021/0085200 A1 3/2021 Auerbach et al.
2021/0085204 A1 3/2021 Auerbach et al.
2021/0085215 A1 3/2021 Auerbach et al.
2021/0085387 A1 3/2021 Amit et al.
2021/0093292 A1 4/2021 Baram et al.
2021/0093294 A1 4/2021 Shemesh et al.
2021/0093374 A1 4/2021 Govari et al.
2021/0093377 A1 4/2021 Herrera et al.
2021/0100612 A1 4/2021 Baron et al.
2021/0113822 A1 4/2021 Beeckler et al.
2021/0127999 A1 5/2021 Govari et al.
2021/0128010 A1 5/2021 Govari et al.
2021/0133516 A1 5/2021 Govari et al.
2021/0145282 A1 5/2021 Bar-Tal et al.
2021/0161592 A1 6/2021 Altmann et al.
2021/0162210 A1 6/2021 Altmann et al.
2021/0169421 A1 6/2021 Govari
2021/0169550 A1 6/2021 Govari et al.
2021/0169567 A1 6/2021 Govari et al.
2021/0169568 A1 6/2021 Govari et al.
2021/0177294 A1 6/2021 Gliner et al.
2021/0177356 A1 6/2021 Gliner et al.
2021/0177503 A1 6/2021 Altmann et al.
2021/0178166 A1 6/2021 Govari et al.
2021/0186363 A1 6/2021 Gliner et al.
2021/0186604 A1 6/2021 Altmann et al.
2021/0196372 A1 7/2021 Altmann et al.
2021/0196394 A1 7/2021 Govari et al.
2021/0212591 A1 7/2021 Govari et al.
2021/0219904 A1 7/2021 Yarnitsky et al.
2021/0278936 A1 9/2021 Katz et al.
2021/0282659 A1 9/2021 Govari et al.
2021/0307815 A1 10/2021 Govari et al.
2021/0308424 A1 10/2021 Beeckler et al.
2021/0338319 A1 11/2021 Govari et al.
2023/0012307 A1* 1/2023 Harlev ............... A61B 18/1492
2023/0225789 A1 7/2023 Okarski et al.

FOREIGN PATENT DOCUMENTS

DE 202023102290 U1 8/2023
DE 202023102282 U1 9/2023
EP 0668740 A1 8/1995
EP 0644738 B1 3/2000
EP 0727183 B1 11/2002
EP 0727184 B1 12/2002
EP 2699153 A1 2/2014
EP 2783651 A1 10/2014
EP 2699151 B1 11/2015
EP 2699152 B1 11/2015
EP 2498706 B1 4/2016
EP 2578173 B1 6/2017
EP 3238645 A1 11/2017
EP 2884931 B1 1/2018
EP 3241493 B1 2/2019
EP 2349440 B1 8/2019
EP 3318211 B1 12/2019
EP 3581135 A1 12/2019
EP 2736434 B1 2/2020
EP 3451962 B1 3/2020
EP 3972510 A1 3/2022
WO 9421167 A1 9/1994
WO 9421169 A1 9/1994
WO 9625095 A1 8/1996
WO 9634560 A1 11/1996
WO 0182814 A2 5/2002
WO 2004087249 A2 10/2004
WO 2012100185 A2 7/2012
WO 2013052852 A1 4/2013
WO 2013162884 A1 10/2013
WO 2013173917 A1 11/2013
WO 2013176881 A1 11/2013
WO 2014176205 A1 10/2014
WO 2016019760 A1 2/2016

(56) References Cited

FOREIGN PATENT DOCUMENTS

| | | | |
|---|---|---|---|
| WO | 2016044687 | A1 | 3/2016 |
| WO | 2017066087 | A1 | 4/2017 |
| WO | 2018111600 | A1 | 6/2018 |
| WO | 2018191149 | A1 | 10/2018 |
| WO | 2019084442 | A1 | 5/2019 |
| WO | 2019143960 | A1 | 7/2019 |
| WO | 2020026217 | A1 | 2/2020 |
| WO | 2020206328 | A1 | 10/2020 |
| WO | 2021126980 | A1 | 6/2021 |

* cited by examiner

MEDICAL DEVICE WITH AN END EFFECTOR INCLUDING CONNECTING HUBS AND AN ELECTRODE ARRAY

FIELD

The present technology relates generally to medical devices, and in particular medical probes with electrodes, and further relates to, but not exclusively, medical probes suitable for use to induce irreversible electroporation (IRE) of cardiac tissues.

BACKGROUND

Cardiac arrhythmias, such as atrial fibrillation (AF), occur when regions of cardiac tissue abnormally conduct electric signals to adjacent tissue. This disrupts the normal cardiac cycle and causes asynchronous rhythm. Certain procedures exist for treating arrhythmia, including surgically disrupting the origin of the signals causing the arrhythmia and disrupting the conducting pathway for such signals. By selectively ablating cardiac tissue by application of energy via a catheter, it is sometimes possible to cease or modify the propagation of unwanted electrical signals from one portion of the heart to another.

Many current ablation approaches in the art utilize radiofrequency (RF) electrical energy to heat tissue. RF ablation can have certain risks related to thermal heating which can lead to tissue charring, burning, steam pop, phrenic nerve palsy, pulmonary vein stenosis, and esophageal fistula.

Cryoablation is an alternative approach to RF ablation that generally reduces thermal risks associated with RF ablation. Maneuvering cryoablation devices and selectively applying cryoablation, however, is generally more challenging compared to RF ablation; therefore, cryoablation is not viable in certain anatomical geometries which may be reached by electrical ablation devices.

Some ablation approaches use irreversible electroporation (IRE) to ablate cardiac tissue using nonthermal ablation methods. IRE delivers short pulses of high voltage to tissues and generates an unrecoverable permeabilization of cell membranes. Delivery of IRE energy to tissues using multi-electrode probes was previously proposed in the patent literature. Examples of systems and devices configured for IRE ablation are disclosed in U.S. Patent Pub. No. 2021/0169550A1, 2021/0169567A1, 2021/0169568A1, 2021/0161592A1, 2021/0196372A1, 2021/0177503A1, and 2021/0186604A1, each of which are incorporated herein by reference.

Basket-style end effectors include spines that must be held in place at their distal portions for proper functioning thereof. There is a need for improved techniques to retain the distal/proximal portions of the spines. There is also a need for large-size basket catheters for pulmonary vein isolation (PVI) using IRE.

SUMMARY

There is provided, in accordance with the disclosed technology, an end effector for a medical device. The end effector can include a plurality of spines extending along a longitudinal axis and configured to move between an expanded configuration and a collapsed configuration. Each spine comprises a proximal end and a distal end. The end effector can include a plurality of electrodes connected to each spine. The end effector can include a connecting hub defining a hub lumen and comprising a first terminal end, a second terminal end, and a plurality of recesses. The plurality of recesses are radially disposed about an outer circumferential surface of the connecting hub and extend parallel to the longitudinal axis. Each recess is open along the longitudinal axis at or proximal the first terminal end. Each recess mates with one of the proximal end and the distal end of a respective spine of plurality of spines to prevent relative movement between the connecting hub and the spine. The end effector can further include an actuator member connected to the connecting hub and the plurality of spines so that translation of actuator member along the longitudinal axis moves the spines from the expanded to the collapsed configuration.

There is further provided, in accordance with the disclosed technology, a connecting hub for use with an end effector of a medical device. The connecting hub can include a first terminal end, a second terminal end opposite the first terminal end, a cylindrical body, and a plurality of recesses. The cylindrical body defines a hub lumen and extends along a longitudinal axis from the first terminal end to the second terminal end. The plurality of recesses are radially disposed about an outer circumferential surface of the cylindrical body and extend parallel to the longitudinal axis. Each recess is open along the longitudinal axis at or proximal the first terminal end, and each recess is configured to mate with a proximal end or a distal end of a spine of the end effector.

DETAILED DESCRIPTION

Figure 1:
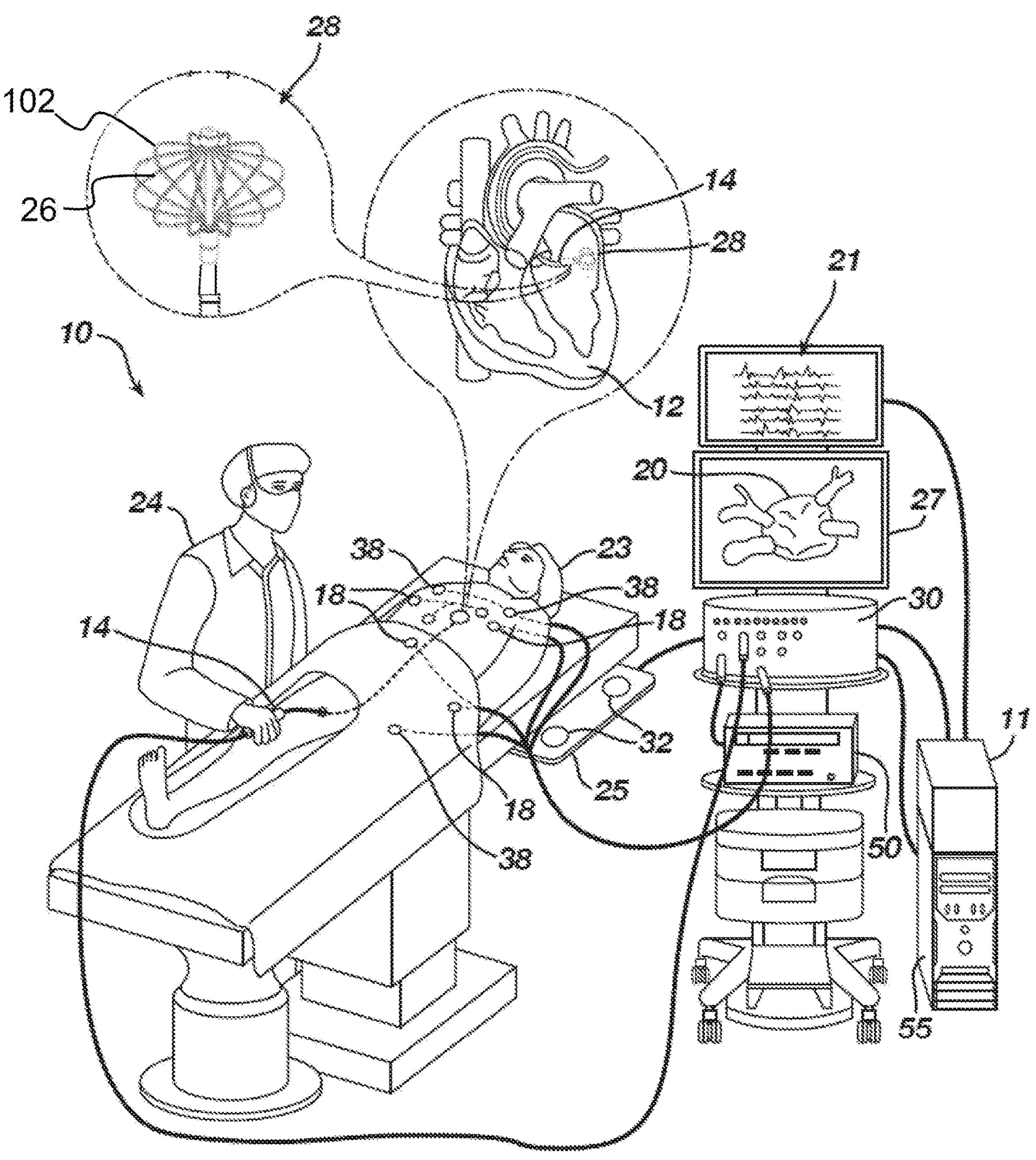
FIG. 1 is a schematic pictorial illustration of a medical system including a medical device with a distal end that includes a medical probe with electrodes, in accordance with the disclosed technology.

The following detailed description should be read with reference to the drawings, in which like elements in different drawings are identically numbered. The drawings, which are not necessarily to scale, depict selected examples and are not intended to limit the scope of the present disclosure. The detailed description illustrates by way of example, not by way of limitation, the principles of the disclosed technology. This description will clearly enable one skilled in the art to make and use the disclosed technology, and describes several embodiments, adaptations, variations, alternatives and uses of the disclosed technology, including what is presently believed to be the best mode of carrying out the disclosed technology.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 110%. In addition, as used herein, the terms "patient," "host," "user," and "subject" refer to any human or animal subject and are not intended to limit the systems or methods to human use, although use of the subject technology in a human patient represents a preferred embodiment. As well, the term "proximal" indicates a location closer to the operator or physician whereas "distal" indicates a location further away to the operator or physician.

As discussed herein, vasculature of a "patient," "host," "user," and "subject" can be vasculature of a human or any animal. It should be appreciated that an animal can be a variety of any applicable type, including, but not limited thereto, mammal, veterinarian animal, livestock animal or pet type animal, etc. As an example, the animal can be a laboratory animal specifically selected to have certain characteristics similar to a human (e.g., rat, dog, pig, monkey, or the like). It should be appreciated that the subject can be any applicable human patient, for example.

As discussed herein, "operator" can include a doctor, surgeon, technician, scientist, or any other individual or delivery instrumentation associated with delivery of a multi-electrode catheter for the treatment of drug refractory atrial fibrillation to a subject.

As discussed herein, the term "ablate" or "ablation", as it relates to the devices and corresponding systems of this disclosure, refers to components and structural features configured to reduce or prevent the generation of erratic cardiac signals in the cells by utilizing non-thermal energy, such as irreversible electroporation (IRE), referred throughout this disclosure interchangeably as pulsed electric field (PEF) and pulsed field ablation (PFA). Ablating or ablation as it relates to the devices and corresponding systems of this disclosure is used throughout this disclosure in reference to non-thermal ablation of cardiac tissue for certain conditions including, but not limited to, arrhythmias, atrial flutter ablation, pulmonary vein isolation, supraventricular tachycardia ablation, and ventricular tachycardia ablation. The term "ablate" or "ablation" also includes known methods, devices, and systems to achieve various forms of bodily tissue ablation as understood by a person skilled in the relevant art.

As discussed herein, the terms "bipolar" and "unipolar" when used to refer to ablation schemes describe ablation schemes which differ with respect to electrical current path and electric field distribution. "Bipolar" refers to ablation scheme utilizing a current path between two electrodes that are both positioned at a treatment site; current density and electric flux density is typically approximately equal at each of the two electrodes. "Unipolar" refers to ablation scheme utilizing a current path between two electrodes where one electrode having a high current density and high electric flux density is positioned at a treatment site, and a second electrode having comparatively lower current density and lower electric flux density is positioned remotely from the treatment site.

As discussed herein, the terms "tubular", "tube" and "shaft" are to be construed broadly and are not limited to a structure that is a right cylinder or strictly circumferential in cross-section or of a uniform cross-section throughout its length. For example, the tubular/shaft structures are generally illustrated as a substantially right cylindrical structure. However, the tubular/shaft structures may have a tapered or curved outer surface without departing from the scope of the present disclosure.

The present disclosure is related to systems, method or uses and devices for IRE ablation of cardiac tissue to treat cardiac arrhythmias. Ablative energies are typically provided to cardiac tissue by a tip portion of a catheter which can deliver ablative energy alongside the tissue to be ablated. Some example catheters include three-dimensional structures at the tip portion and are configured to administer ablative energy from various electrodes positioned on the three-dimensional structures. Ablative procedures incorporating such example catheters can be visualized using fluoroscopy.

Ablation of cardiac tissue using application of a thermal technique, such as radio frequency (RF) energy and cryoablation, to correct a malfunctioning heart is a well-known procedure. Typically, to successfully ablate using a thermal technique, cardiac electropotentials need to be measured at various locations of the myocardium. In addition, temperature measurements during ablation provide data enabling the efficacy of the ablation. Typically, for an ablation procedure using a thermal technique, the electropotentials and the temperatures are measured before, during, and after the actual ablation. RF approaches can have risks that can lead to tissue charring, burning, steam pop, phrenic nerve palsy, pulmonary vein stenosis, and esophageal fistula. Cryoablation is an alternative approach to RF ablation that can reduce some thermal risks associated with RF ablation. However maneuvering cryoablation devices and selectively applying cryoablation is generally more challenging compared to RF ablation; therefore, cryoablation is not viable in certain anatomical geometries which may be reached by electrical ablation devices.

The present disclosure can include electrodes configured for irreversible electroporation (IRE), RF ablation, and/or cryoablation. IRE can be referred to throughout this disclosure interchangeably as pulsed electric field (PEF) ablation and pulsed field ablation (PFA). IRE as discussed in this disclosure is a non-thermal cell death technology that can be used for ablation of atrial arrhythmias. To ablate using IRE/PEF, biphasic voltage pulses are applied to disrupt cellular structures of myocardium. The biphasic pulses are non-sinusoidal and can be tuned to target cells based on electrophysiology of the cells. In contrast, to ablate using RF, a sinusoidal voltage waveform is applied to produce heat at the treatment area, indiscriminately heating all cells in the treatment area. IRE therefore has the capability to spare adjacent heat sensitive structures or tissues which would be of benefit in the reduction of possible complications known with ablation or isolation modalities. Additionally, or alternatively, monophasic pulses can be utilized.

Electroporation can be induced by applying a pulsed electric field across biological cells to cause reversable (temporary) or irreversible (permanent) creation of pores in the cell membrane. The cells have a transmembrane electrostatic potential that is increased above a resting potential upon application of the pulsed electric field. While the transmembrane electrostatic potential remains below a threshold potential, the electroporation is reversable, meaning the pores can close when the applied pulse electric field is removed, and the cells can self-repair and survive. If the transmembrane electrostatic potential increases beyond the threshold potential, the electroporation is irreversible, and the cells become permanently permeable. As a result, the cells die due to a loss of homeostasis and typically die by apoptosis. Generally, cells of differing types have differing threshold potential. For instance, heart cells have a threshold potential of approximately 500 V/cm, whereas for bone it is 3000 V/cm. These differences in threshold potential allow IRE to selectively target tissue based on threshold potential.

The technology of this disclosure includes systems and methods for applying electrical signals from catheter electrodes positioned in the vicinity of myocardial tissue to generate a generate ablative energy to ablate the myocardial tissue. In some examples, the systems and methods can be effective to ablate targeted tissue by inducing irreversible electroporation. In some examples, the systems and methods can be effective to induce reversible electroporation as part of a diagnostic procedure. Reversible electroporation occurs when the electricity applied with the electrodes is below the electric field threshold of the target tissue allowing cells to repair. Reversible electroporation does not kill the cells but allows a physician to see the effect of reversible electroporation on electrical activation signals in the vicinity of the target location. Example systems and methods for reversible electroporation is disclosed in U.S. Patent Publication 2021/0162210, the entirety of which is incorporated herein by reference.

The pulsed electric field, and its effectiveness to induce reversible and/or irreversible electroporation, can be affected by physical parameters of the system and biphasic pulse parameters of the electrical signal. Physical parameters can include electrode contact area, electrode spacing, electrode geometry, etc. Examples presented herein generally include physical parameters adapted to effectively induce reversible and/or irreversible electroporation. Biphasic pulse parameters of the electrical signal can include voltage amplitude, pulse duration, pulse interphase delay, inter-pulse delay, total application time, delivered energy, etc. In some examples, parameters of the electrical signal can be adjusted to induce both reversible and irreversible electroporation given the same physical parameters. Examples of various systems and methods of ablation including IRE are presented in U.S. Patent Publications 2021/0169550A1, 2021/0169567A1, 2021/0169568A1, 2021/0161592A1, 2021/0196372A1, 2021/0177503A1, and 2021/0186604A1, the entireties of each of which are incorporated herein by reference.

Reference is made to FIG. 1 showing an example catheter-based electrophysiology mapping and ablation system 10. System 10 includes multiple catheters, which are percutaneously inserted by physician 24 through the patient's 23 vascular system into a chamber or vascular structure of a heart 12. Typically, a delivery sheath catheter is inserted into the left or right atrium near a desired location in heart 12. Thereafter, a plurality of catheters can be inserted into the delivery sheath catheter so as to arrive at the desired location. The plurality of catheters may include catheters dedicated for sensing Intracardiac Electrogram (IEGM) signals, catheters dedicated for ablating and/or catheters dedicated for both sensing and ablating. An example medical device/probe, e.g., a catheter 14, that is configured for sensing IEGM is illustrated herein. Physician 24 brings a distal tip of catheter 14 (i.e., a basket assembly 28 in this case) into contact with the heart wall for sensing a target site in heart 12. A catheter 14 with a distal basket assembly can be referred to as a basket catheter. For ablation, physician 24 would similarly bring a distal end of an ablation catheter to a target site for ablating.

Catheter 14 is an exemplary catheter that includes one and preferably multiple electrodes 26 optionally distributed over a plurality of spines 104 at basket assembly 28 and configured to sense the IEGM signals. Catheter 14 may additionally include a position sensor embedded in or near basket assembly 28 for tracking position and orientation of basket assembly 28. Optionally and preferably, position sensor is a magnetic based position sensor including three magnetic coils for sensing three-dimensional (3D) position and orientation.

Magnetic based position sensor may be operated together with a location pad 25 including a plurality of magnetic coils 32 configured to generate magnetic fields in a predefined working volume. Real time position of basket assembly 28 of catheter 14 may be tracked based on magnetic fields generated with location pad 25 and sensed by magnetic based position sensor. Details of the magnetic based position sensing technology are described in U.S. Pat. Nos. 5,391,199; 5,443,489; 5,558,091; 6,172,499; 6,239,724; 6,332,089; 6,484,118; 6,618,612; 6,690,963; 6,788,967; 6,892,091, each of which are incorporated herein by reference.

System 10 includes one or more electrode patches 38 positioned for skin contact on patient 23 to establish location reference for location pad 25 as well as impedance-based tracking of electrodes 26. For impedance-based tracking, electrical current is directed toward electrodes 26 and sensed at electrode skin patches 38 so that the location of each electrode can be triangulated via the electrode patches 38. Details of the impedance-based location tracking technology are described in U.S. Pat. Nos. 7,536,218; 7,756,576; 7,848,787; 7,869,865; and 8,456,182, each of which are incorporated herein by reference.

A recorder 11 displays electrograms 21 captured with body surface ECG electrodes 18 and intracardiac electrograms (IEGM) captured with electrodes 26 of catheter 14. Recorder 11 may include pacing capability for pacing the heart rhythm and/or may be electrically connected to a standalone pacer.

System 10 may include an ablation energy generator 50 that is adapted to conduct ablative energy to one or more of electrodes at a distal tip of a catheter configured for ablating. Energy produced by ablation energy generator 50 may include, but is not limited to, radiofrequency (RF) energy or pulsed-field ablation (PFA) energy, including monopolar or bipolar high-voltage DC pulses as may be used to effect irreversible electroporation (IRE), or combinations thereof.

Patient interface unit (PIU) 30 is an interface configured to establish electrical communication between catheters, electrophysiological equipment, power supply and a workstation 55 for controlling operation of system 10. Electrophysiological equipment of system 10 may include for example, multiple catheters, location pad 25, body surface ECG electrodes 18, electrode patches 38, ablation energy generator 50, and recorder 11. Optionally and preferably, PIU 30 additionally includes processing capability for implementing real-time computations of location of the catheters and for performing ECG calculations.

Workstation 55 includes memory, processor unit with memory or storage with appropriate operating software loaded therein, and user interface capability. Workstation 55 may provide multiple functions, optionally including (1) modeling the endocardial anatomy in three-dimensions (3D) and rendering the model or anatomical map 20 for display on a display device 27, (2) displaying on display device 27 activation sequences (or other data) compiled from recorded electrograms 21 in representative visual indicia or imagery superimposed on the rendered anatomical map 20, (3) displaying real-time location and orientation of multiple catheters within the heart chamber, and (5) displaying on display device 27 sites of interest such as places where ablation energy has been applied. One commercial product embodying elements of the system 10 is available as the CARTO™ 3 System, available from Biosense Webster, Inc., 31 Technology Drive, Suite 200, Irvine, CA 92618 USA.

Figure 2:
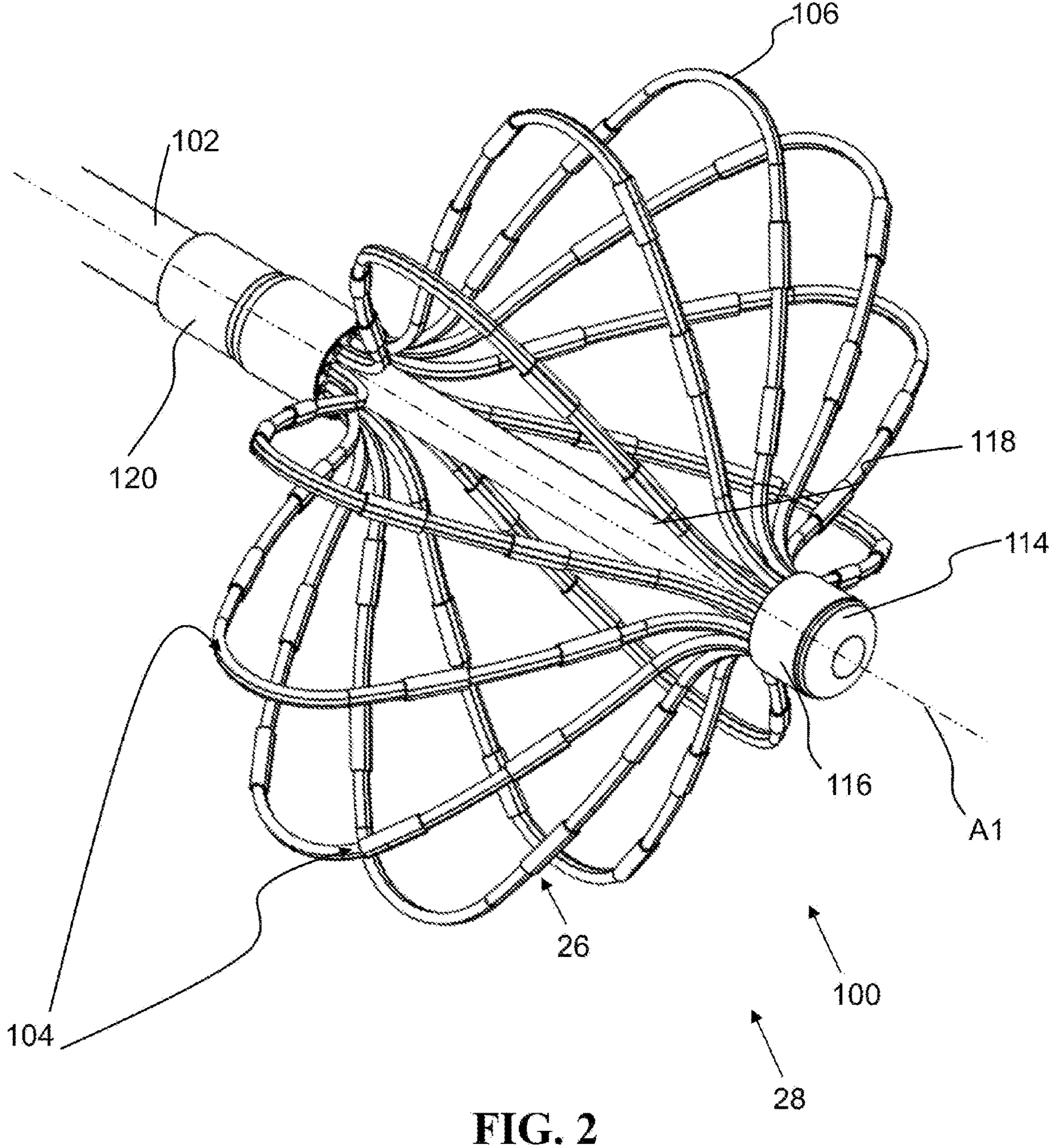
FIG. 2 is a schematic pictorial illustration showing a perspective view of an end effector of the medical device, in accordance with the disclosed technology.

FIG. 2 is a schematic pictorial illustration showing a perspective view of an end effector of a medical device 14, such as a medical probe, with electrodes 26. The medical device 14 includes, at its distal tip 28, the end effector 100. The end effector 100 in the presently described example takes the form of a basket assembly that includes at least one spine 104. Spines 104 may have elliptical (e.g., circular) or rectangular (that may appear to be flat) cross-sections, and include a flexible, resilient material (e.g., a shape-memory alloy such as nickel-titanium, also known as Nitinol) forming a strut. The spines 104 can be formed from a planar or cylindrical tube stock of material using any suitable method. For example, the spines 104 can be formed by cutting, laser cutting, stamping, etc. The spines 104 have a distal end 104A (FIG. 4) and a proximal end 104B (FIG. 6) and extend along a longitudinal axis A1. The spine(s) 104 are movable between an expanded configuration and a collapsed configuration via an actuator member. The actuator member is connected/coupled to the spines such that translation of the actuator member along the longitudinal axis moves the spines from the expanded position to the collapsed position.

In examples described herein, electrodes 26 can be configured to deliver ablation energy (IRE and/or RF) to tissue in heart 12. In FIG. 2, each spine 104 has a midpoint (e.g., the approximate point where the spine 104 bends from extending away from the longitudinal axis A1 to towards it), and there are four electrodes 26 connected to each spine. A first two of the four electrodes 26 are disposed on a first side of the midpoint of each spine 104 and a second two of the four electrodes 26 are disposed on a second side of the midpoint of each spine 104. In addition to using electrodes 26 to deliver ablation energy, the electrodes 26 can also be used to determine the location of the end effector 100 and/or to measure a physiological property such as local surface electrical potentials at respective locations on tissue in heart 12. The electrodes 26 can be biased such that a greater portion of the electrode 26 faces outwardly from the end effector 100 such that the electrodes 26 deliver a greater amount of electrical energy outwardly away from the end effector 100 (i.e., toward the heart 12 tissue) than inwardly toward the end effector 100.

Examples of materials ideally suited for forming electrodes 26 include gold, platinum, and palladium (and their respective alloys). These materials also have high thermal conductivity which allows the minimal heat generated on the tissue (i.e., by the ablation energy delivered to the tissue) to be conducted through the electrodes to the back side of the electrodes (i.e., the portions of the electrodes on the inner sides of the spines), and then to the blood pool in heart 12.

The end effector 100 is connected to the rest of the medical probe 14 via an elongated shaft 102. The elongated shaft 102 connects the end effector 100 to a handle that, in use, the operator 24 can manipulate. The elongated shaft 102 can be tubular in form and flexible, with certain portions being more flexible than others. For example, a tip portion thereof can be made more flexible than the rest to allow the end effector 100 to be easily deflected. The elongated shaft 102 can be formed from a flexible, biocompatible electrically insulative material such as polyamide-polyether (Pebax) copolymers, polyethylene terephthalate (PET), urethanes, polyimide, parylene, silicone, etc. In some examples, insulative material can include biocompatible polymers including, without limitation, polyetheretherketone (PEEK), polyglycolic acid (PGA), poly(lactic-co-glycolic acid) copolymer (PLGA), polycaprolactive (PCL), poly(3-hydroxybutyrate-co-3-hydroxyvalerate) (PHBV), poly-L-lactide, polydioxanone, polycarbonates, and polyanhydrides with the ratio of certain polymers being selected to control the degree of inflammatory response. Moreover, a flexible sleeve 120 is provided over the proximal end of the end effector 100 for further enhance the atraumaticity of the end effector 100.

A connector tube or rod 118 is connected to the distal end 104A of the spines. In some examples, the connector tube 118 functions as the actuator member to facilitate the expanding and collapsing of the spines 104. For example, as discussed above, the connector tube 118 can be translated along a longitudinal axis A1 to expand/collapse the spines 104. In the expanded configuration (e.g., FIG. 2) as well as the collapsed configuration, one or more spines 104 can bow radially outwardly from the longitudinal axis A1. Alternatively, another actuator member (e.g., a pull wire) can be used in conjunction with the connector tube 118, with the connector tube/rod 118 being used for other purposes, such as for routing irrigation. For example, the connector tube 118 can include a plurality of irrigation holes along its length or provide passage for other irrigation tubes. The connector tube can also include a reference or return electrode connected thereto. The spine(s) 104, elongated shaft 102, and connector tube 118 are arranged generally along (i.e., parallel to or coaxial with) the longitudinal axis A1 when the elongated shaft 200 is unbent. The connector tube 118 also defines a lumen 118A (FIG. 3), which is coaxial with the longitudinal axis A1, and through which various medical devices can be extended therethrough when in use, such as a mapping catheter or a guidewire.

An atraumatic annulus 114 and coil 116 are connected to the distal end 104A of the spines 104. In some examples, the coil 116 can comprise a single axis sensor (SAS). In other examples, the coil 116 can comprise a dual axis sensor (DAS) or a triple axis sensor (TAS). The coil 116 can comprise a conductive material wound in a coil or a coil formed into a flexible circuit. The coil 116 can comprise electrical leads for conduction of current induced on the coil to the patient interface unit 30. As will be appreciated, by attaching a coil 116 to the distal end of the end effector 100, it is possible to detect a position thereof. In this way, a physician 24 can more accurately determine the position of the distal end of the end effector 100 before applying ablative energy to tissue.

An insulative material, referred to herein as a jacket 106, is provided over each spine 104. Each jacket 106 serves to enhance the atraumaticity of the end effector 100 to protect the subject from sharp edges and for irrigation purposes described in greater detail below. The jacket 106 can include a polymer. For example, the jacket 106 can be formed from a flexible, biocompatible electrically insulative material such as polyamide-polyether (Pebax) copolymers, polyethylene terephthalate (PET), urethanes, polyimide, parylene, silicone, etc. In some examples, insulative material can include biocompatible polymers including, without limitation, polyetheretherketone (PEEK), polyglycolic acid (PGA), poly(lactic-co-glycolic acid) copolymer (PLGA), polycaprolactive (PCL), poly(3-hydroxybutyrate-co-3-hydroxyvalerate) (PHBV), poly-L-lactide, polydioxanone, polycarbonates, and polyanhydrides with the ratio of certain polymers being selected to control the degree of inflammatory response. Furthermore, while the jacket 106 is shown to be tubular in these figures, the jacket 106 can be shaped, scalloped, ribbed, ridged, concaved, convexed, or otherwise configured such that the overall profile of jacket 106 yields physical and/or mechanical properties, such as rigidity and flexion along multiple axes, required by the end effector 100, mentioned above.

Figure 3:
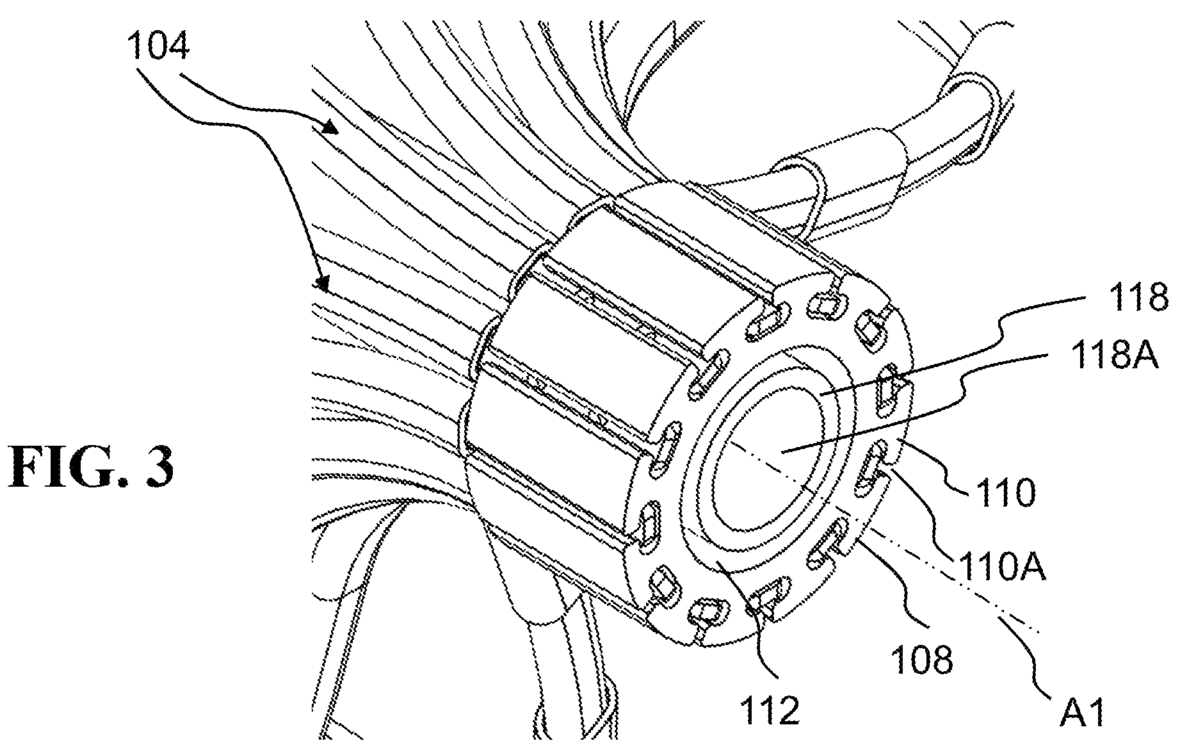
FIG. 3 is a schematic pictorial illustration showing a detail perspective view of the distal end of the end effector, with the coil and annulus removed for clarity, in accordance with the disclosed technology.
Figure 4:
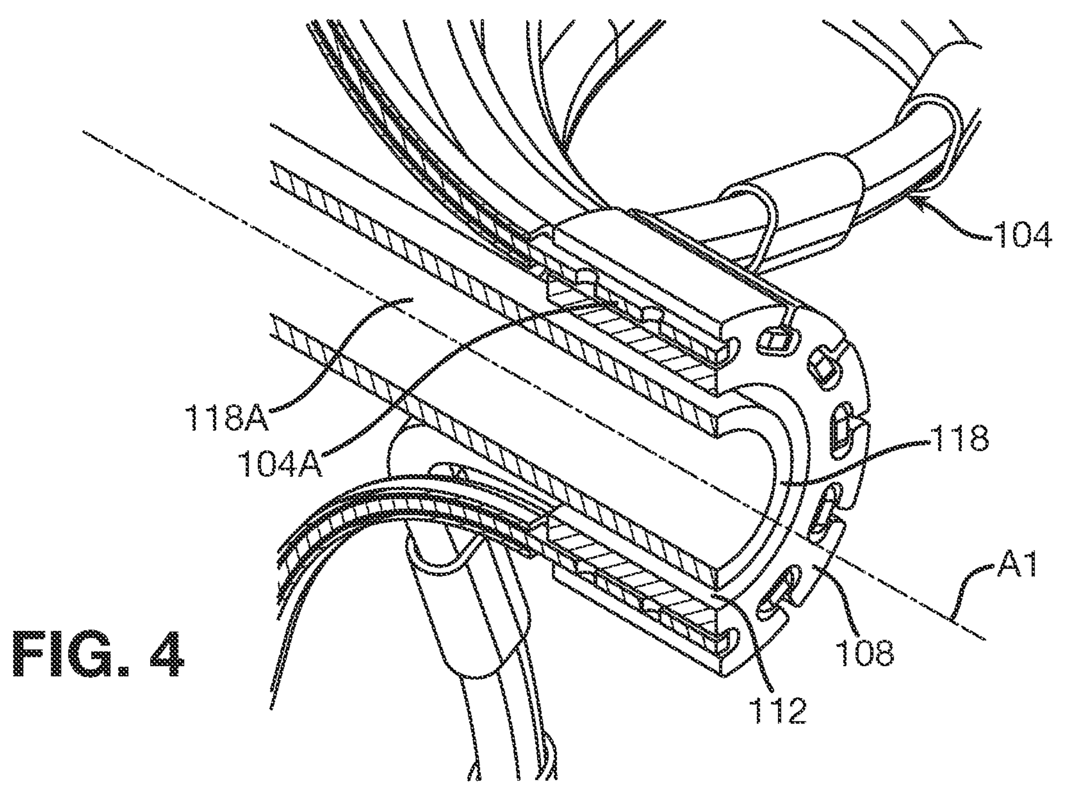
FIG. 4 is a schematic pictorial illustration showing a detail cross-sectional view of the distal end as shown in FIG. 3, cut relative to a vertical plane that intersects the longitudinal axis, in accordance with the disclosed technology.

FIG. 3 is a schematic pictorial illustration showing a detail perspective view of the distal end of the end effector 100, with the coil 116 and annulus 114 removed for clarity. FIG. 4 is a schematic pictorial illustration showing a detail cross-sectional view of the distal end as shown in FIG. 3, cut relative to a vertical plane that intersects the longitudinal axis A1.

Making reference FIGS. 3 and 4, the spines 104 are connected at their distal ends 104A to a distal hub 108, also referred to herein as a connecting hub. The distal hub 108 is a monolithic cylindrical body that defines a distal hub lumen 108 that connects with the connector tube 118. The distal hub 108 can be made from nitinol or any other appropriate bio-compatible material. The distal hub 108 extends from a first terminal end (i.e., left-most end of the distal hub 108 along the longitudinal axis A1, relative to FIG. 3) to a second terminal end (i.e., right-most end of the distal hub 108 along the longitudinal axis A1, relative to FIG. 3) opposite the first terminal end.

Further, the distal hub 108 defines a plurality of upside-down T-shaped recesses 110A that are radially symmetric, are disposed about and defined in an outer circumferential surface of the distal hub 108, and extend parallel to the longitudinal axis A1. As seen in the cross-sectional view of FIG. 4, each recess 110A is open along the longitudinal axis A1 at the first terminal end and the second terminal end (i.e., there is no material defining a termination point to these recesses 110A at these ends). In other words, each recess 110A extends an entire length of the distal hub 108. Moreover, each recess 110A receives the distal end 104A of a respective spine 104 and mates therewith to prevent relative movement between the distal hub 108 and the spine 104. The distal ends 104A are mated with the distal hub 108 by sliding them into the recesses 110A in a direction parallel to the longitudinal axis A1.

With continued reference to FIGS. 3 and 4, adjacent recesses 110A, with their upside-down T-shape, define a T-shaped formation 110 therebetween. The recesses 110A space the T-shaped formations 110 from one another. The upper portions of adjacent T-formations 110 engage an outer face of each respective spine 104 to prevent relative movement therebetween.

Figure 5:
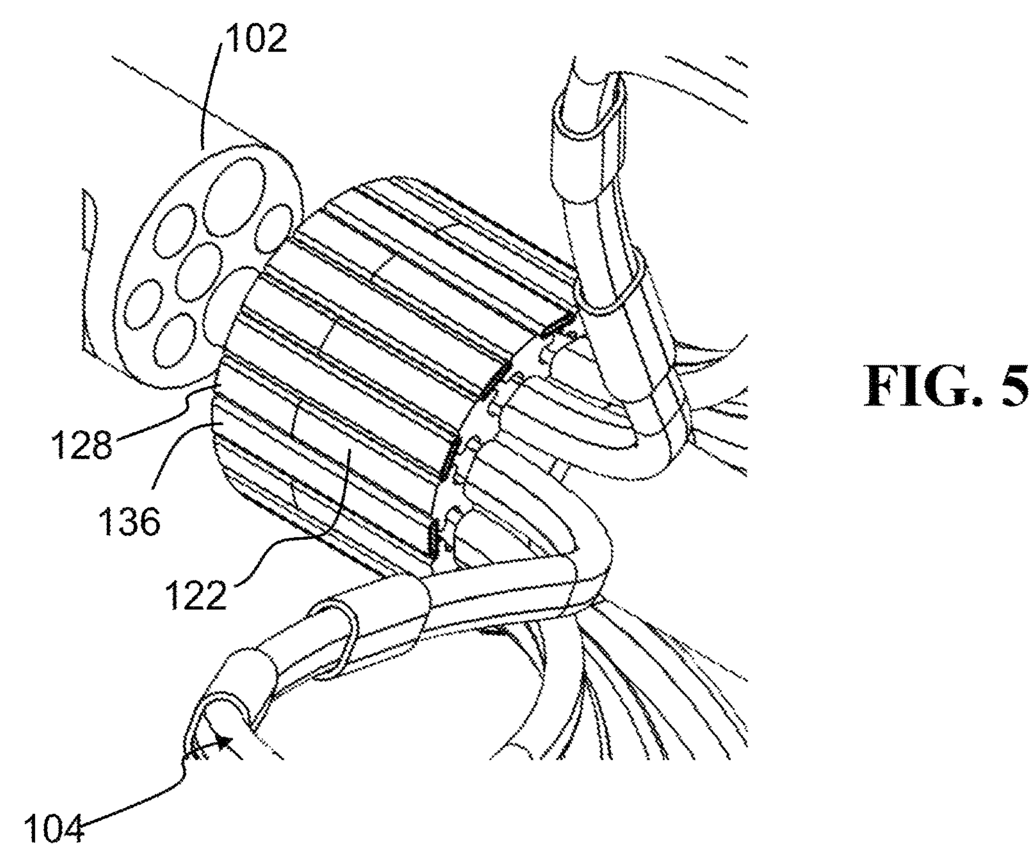
FIG. 5 is a schematic pictorial illustration showing a detail perspective view of the proximal end of the end effector, with the sleeve removed for clarity, in accordance with the disclosed technology.
Figure 6:
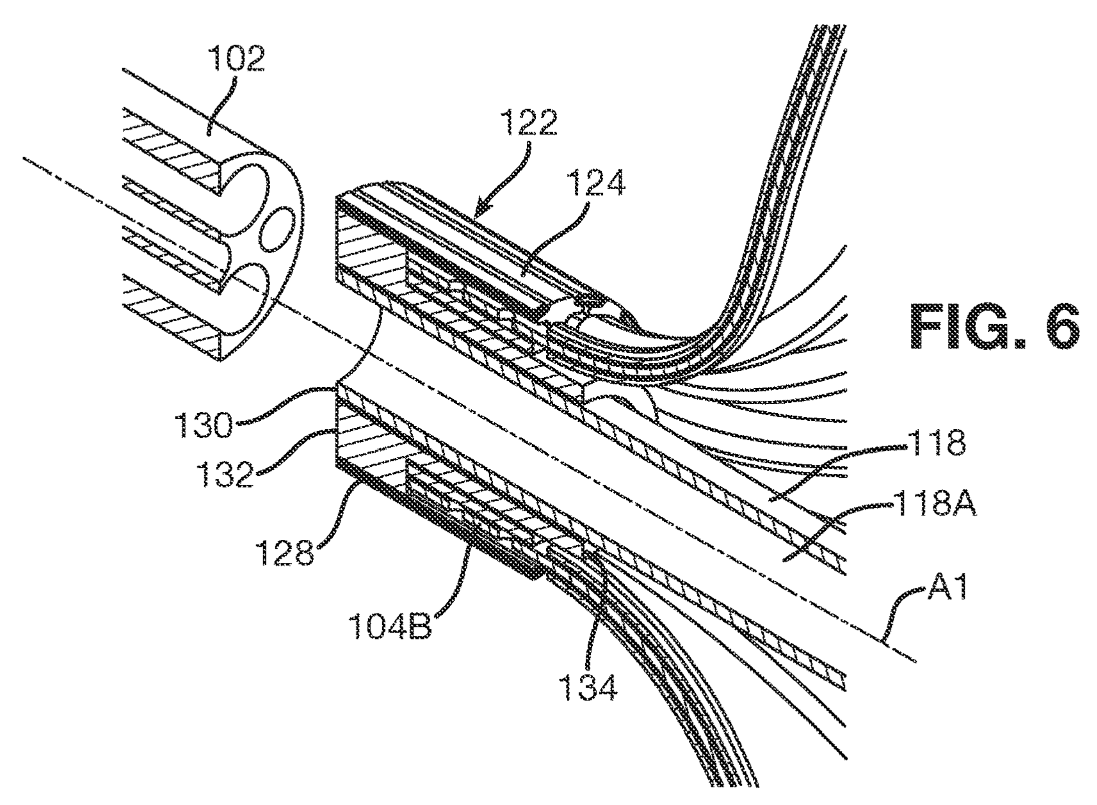
FIG. 6 is a schematic pictorial illustration showing a detail cross-sectional view of the proximal end as shown in FIG. 5, cut relative to a vertical plane that intersects the longitudinal axis, in accordance with the disclosed technology.
Figure 7:
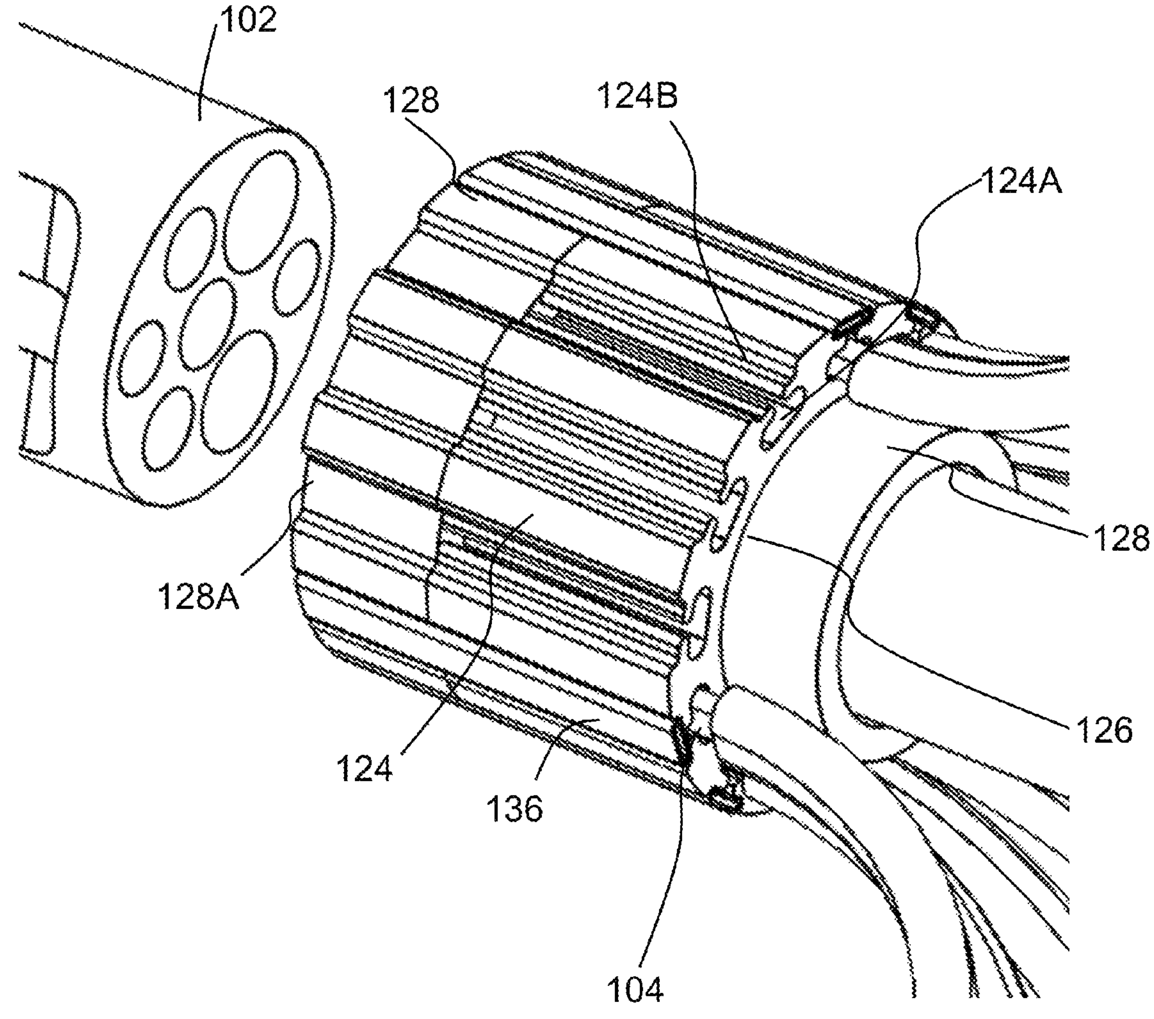
FIG. 7 is a schematic pictorial illustration showing an enlarged detail perspective view of the proximal end shown in FIG. 3, with tubing removed for clarity, in accordance with the disclosed technology.

FIG. 5 is a schematic pictorial illustration showing a detail perspective view of the proximal end of the end effector 100, with the sleeve 120 removed for clarity. FIG. 6 is a schematic pictorial illustration showing a detail cross-sectional view of the proximal end as shown in FIG. 5, cut relative to a vertical plane that intersects the longitudinal axis A1. FIG. 7 is a schematic pictorial illustration showing an enlarged detail perspective view of the proximal end shown in FIG. 3, with tubing 136 removed for clarity (the tubing 136 is discussed in greater detail below).

Making reference primarily FIGS. 5-7, the spines 104 are connected at their proximal ends 104B to a proximal hub 122, also referred to herein as a connecting hub. The proximal hub 122 is a monolithic cylindrical body that defines a proximal hub lumen 126 that indirectly connects with the connector tube 118. The proximal hub 122 can be made from nitinol or any other appropriate bio-compatible material. The proximal hub 122 extends from a first terminal end (i.e., left-most end of the proximal hub 122 along the longitudinal axis A1, relative to FIG. 6) to a second terminal end (i.e., right-most end of the proximal hub 122 along the longitudinal axis A1, relative to FIG. 6) opposite the first terminal end.

Further, similar to the distal end, the proximal hub 122 defines a plurality of upside-down T-shaped recesses 124A that are radially symmetric, are disposed about and defined in an outer circumferential surface of the proximal hub 122, and extend parallel to the longitudinal axis A1. As seen in the cross-sectional view of FIG. 6, each recess 124A (not explicitly labelled in FIG. 6 due to proximal ends 104B being disposed in the recesses 124A, refer to FIG. 7) is open along the longitudinal axis A1 at the first terminal end and the second terminal end (i.e., there is no material defining a termination point to these recesses 124A at these ends). In other words, each recess 124A extends an entire length of the proximal hub 122. Moreover, each recess 124A receives the proximal end 104A of a respective spine 104 and mates therewith to prevent relative movement between the proximal hub 122 and the spine 104. The proximal ends 104B are mated with the proximal hub 122 by sliding them into the recesses 124A in a direction parallel to the longitudinal axis A1. They are held in place in any appropriate manner, e.g., friction fit, fastener(s), adhesive(s), and the like.

With continued reference to FIGS. 5 and 6, adjacent recesses 124A, with their upside-down T-shape, define a T-shaped formation 124 therebetween. The recesses 124A space the T-shaped formations 124 from one another. The upper portions of adjacent T-formations 124 engage an outer face of each respective spine 104 to prevent relative movement therebetween.

In some examples, the proximal hub 122 and distal hub 108 are designed identically to increase the modularity of the connecting hub. In the presently depicted example, and as particularly shown in FIG. 7, opposing upper lateral sides of each T-shaped formation 124 each define a groove 124B. Adjacent grooves 124B of adjacent T-shaped formations 124 form a groove pair. As seen best in FIG. 7, each groove pair is disposed above the respective recess 124A that spaces the respective adjacent T-shaped formations 124. In other words, the groove pairs and recesses 124A are substantially radially aligned with one another.

Additionally at the proximal end of the end effector 100 is a proximal tubular housing 128 that mates with the proximal hub 122 along the longitudinal axis A1. The tubular housing 128 defines a housing lumen 130 through which the connector tube 118 runs. The proximal hub 122 slides over a distal portion of the tubular housing 128 such that the tubular housing 128 extends through the hub lumen 126 of the proximal hub 122. As can also be seen in FIG. 7, an outer surface of the distal portion of the tubular housing 128 are housing grooves 128A that align with the hub grooves 124B along the longitudinal axis A1. Making reference to FIGS. 5 and 7, each hub groove pair 124B and aligned housing groove 128A cooperatively receives an electrical tube 136, through which electrical wires/connections can be routed to electrically connect the end effector 100 to the rest of the system.

Figure 8:
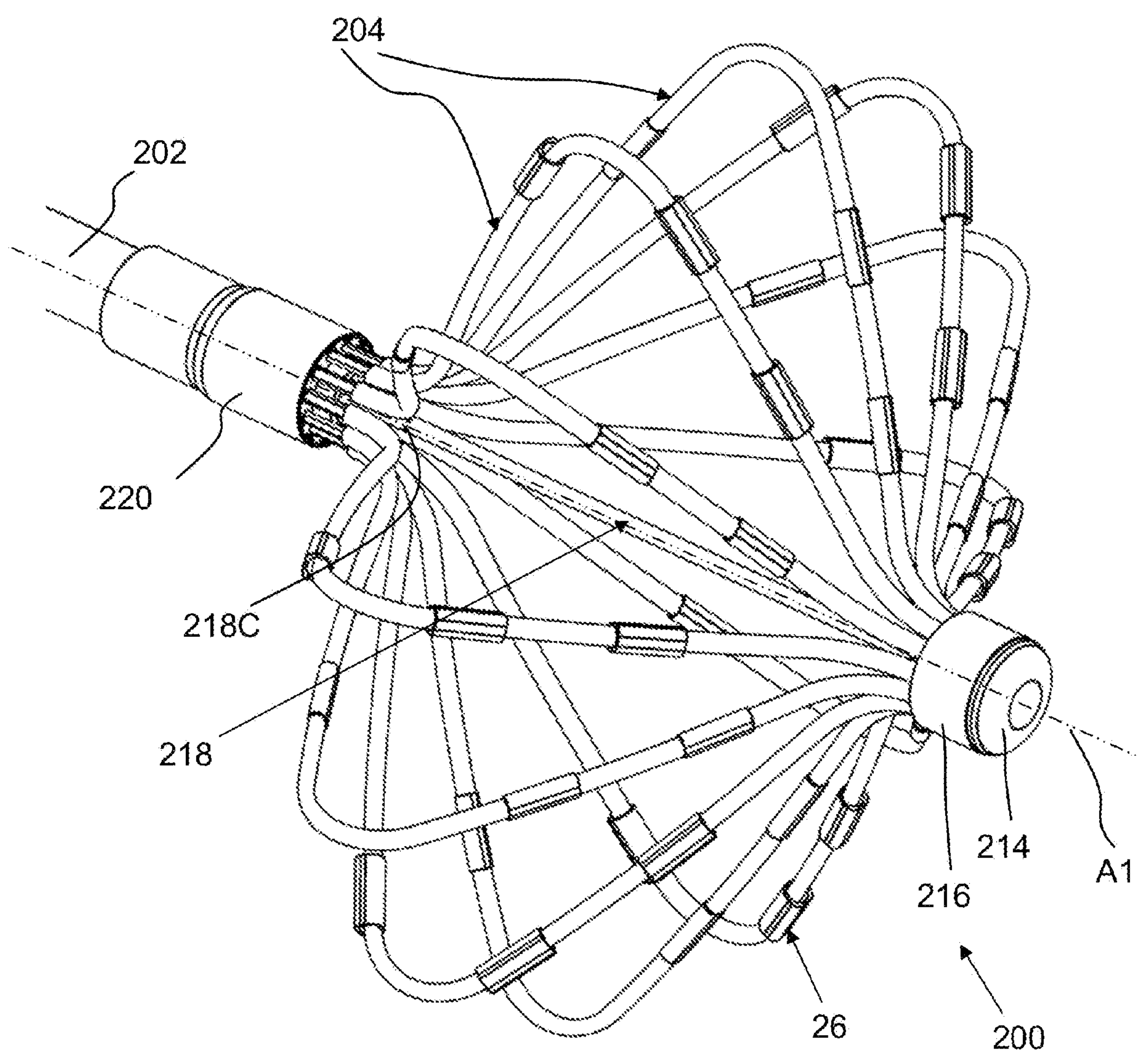
FIG. 8 is a schematic pictorial illustration showing a perspective view of a second end effector, in accordance with the disclosed technology.
Figure 9:
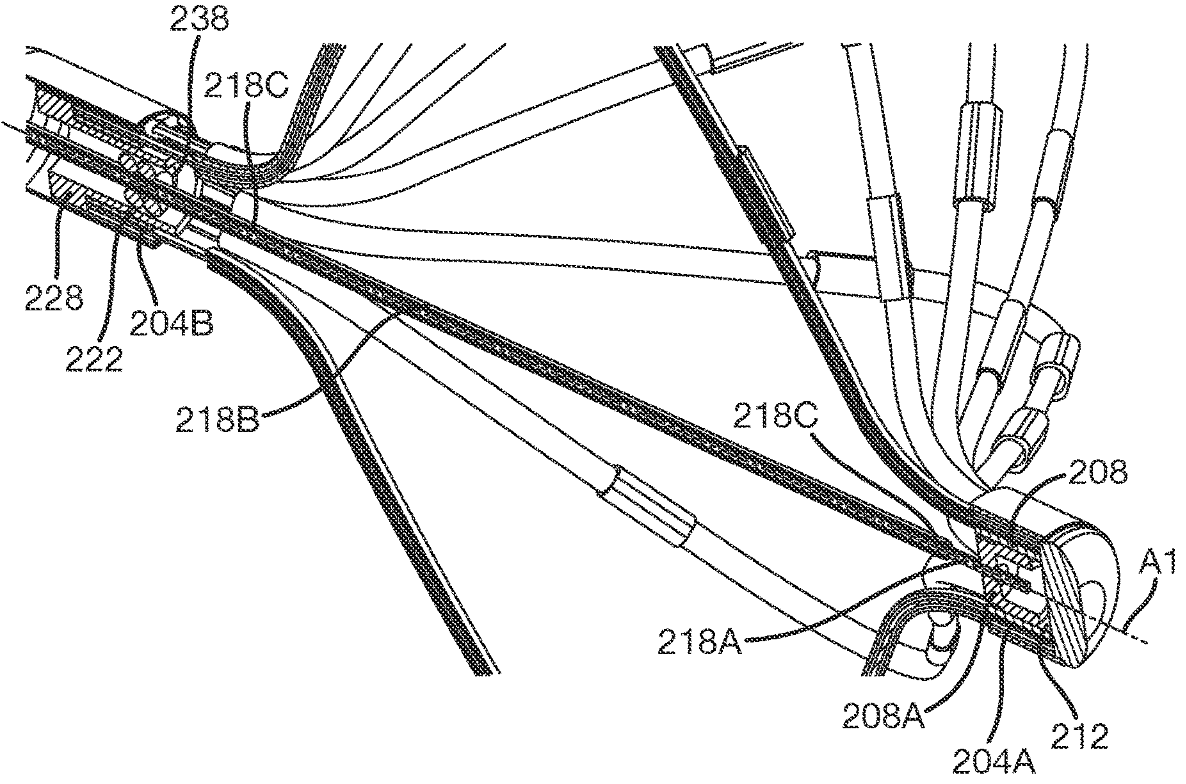
FIG. 9 is a schematic pictorial illustration showing a cross-sectional detail view of the second end effector shown in FIG. 9, cut relative to a vertical plane that intersects the longitudinal axis, with outer regions of the second end effector not shown, in accordance with the disclosed technology.

FIG. 8 is a schematic pictorial illustration showing a perspective view of a second end effector 200. FIG. 9 is a schematic pictorial illustration showing a cross-sectional detail view of the second end effector 200 shown in FIG. 3, cut relative to a vertical plane that intersects the longitudinal axis A1. Details specific to the second end effector 200 that contrast with the first end effector 100 are focused on in the following description. It will be appreciated that many of the features discussed with the first end effector 100 can be appropriately incorporated in the second end effector 200, and vice versa. By way of example, the second end effector 200 can have a similarly or identically designed elongated shaft 202, spines 204 with distal 204A and proximal 204B ends, distal hub 208, distal hub lumen 212, annulus 214, coil 216, proximal sleeve 220, proximal hub 222, and proximal tubular housing 228.

In FIG. 8, each spine 204 has three electrodes 26 positioned thereon such that each three electrodes 26 on each respective spine align with one another from spine 204 to spine 204. In other words, each spine 204 has the electrodes 26 positioned in the same locations along their lengths. With three electrodes 26 on the spine, the electrodes 26 have a total tissue-contacting surface area sufficient to safely deliver PFA pulses of approximately 2000V.

Further to the above, where the second end effector 200 primarily differs is the actuator member 218 that actuates the spines between the collapsed and expanded configuration and/or provides irrigation to around the end effector 200. The actuator member 218 shown a puller wire 218A and includes an irrigation tube 218B. The irrigation tube 218B extends along the longitudinal axis A1. The irrigation tube 218B also includes pores 218C for permitting an irrigation fluid, such as saline, to be distributed around each electrode 26. The puller wire 218A extends through the irrigation tube 218B and connects with the spines 104 such that it can move the spines 104 between the expanded configuration and the collapsed configuration. More specifically, a distal hub fastener 208A (to which the puller wire 218A is attached) is connected within the distal hub lumen 212 to the distal hub 208 which, as discussed above with respect to end effector 100, mates with distal ends 204A of the spines 204. At a proximal side of the end effector 200, within the proximal tubular housing 228, are one or more O-rings 228. The O-rings are configured to maintain the radial positioning of the puller wire 218A relative the longitudinal axis A1 and to permit the puller wire 218A to stably translate back and forth to actuate the spines 204.

Figure 10:
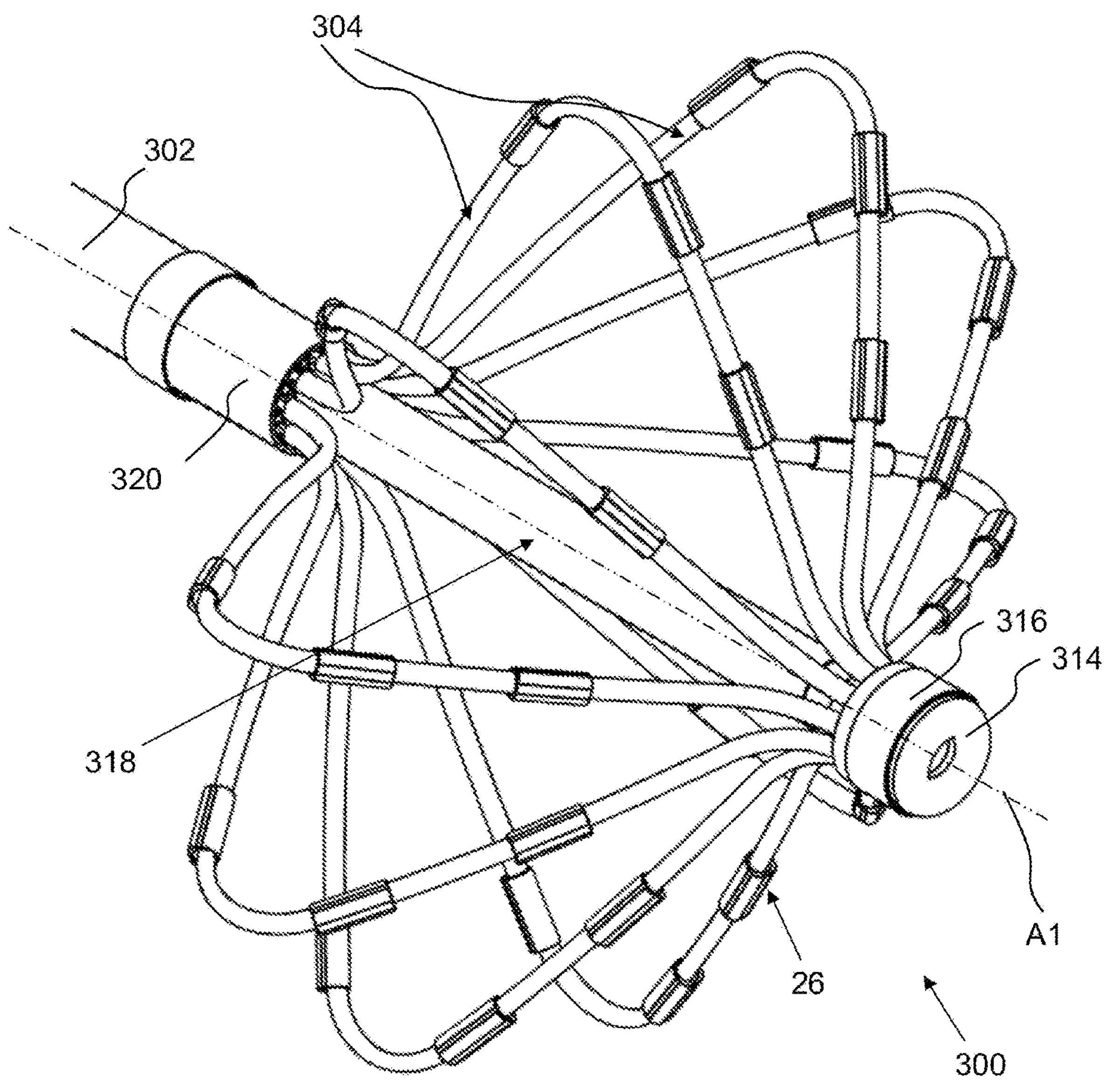
FIG. 10 is a schematic pictorial illustration showing a perspective view of a third end effector, in accordance with the disclosed technology.
Figure 11:
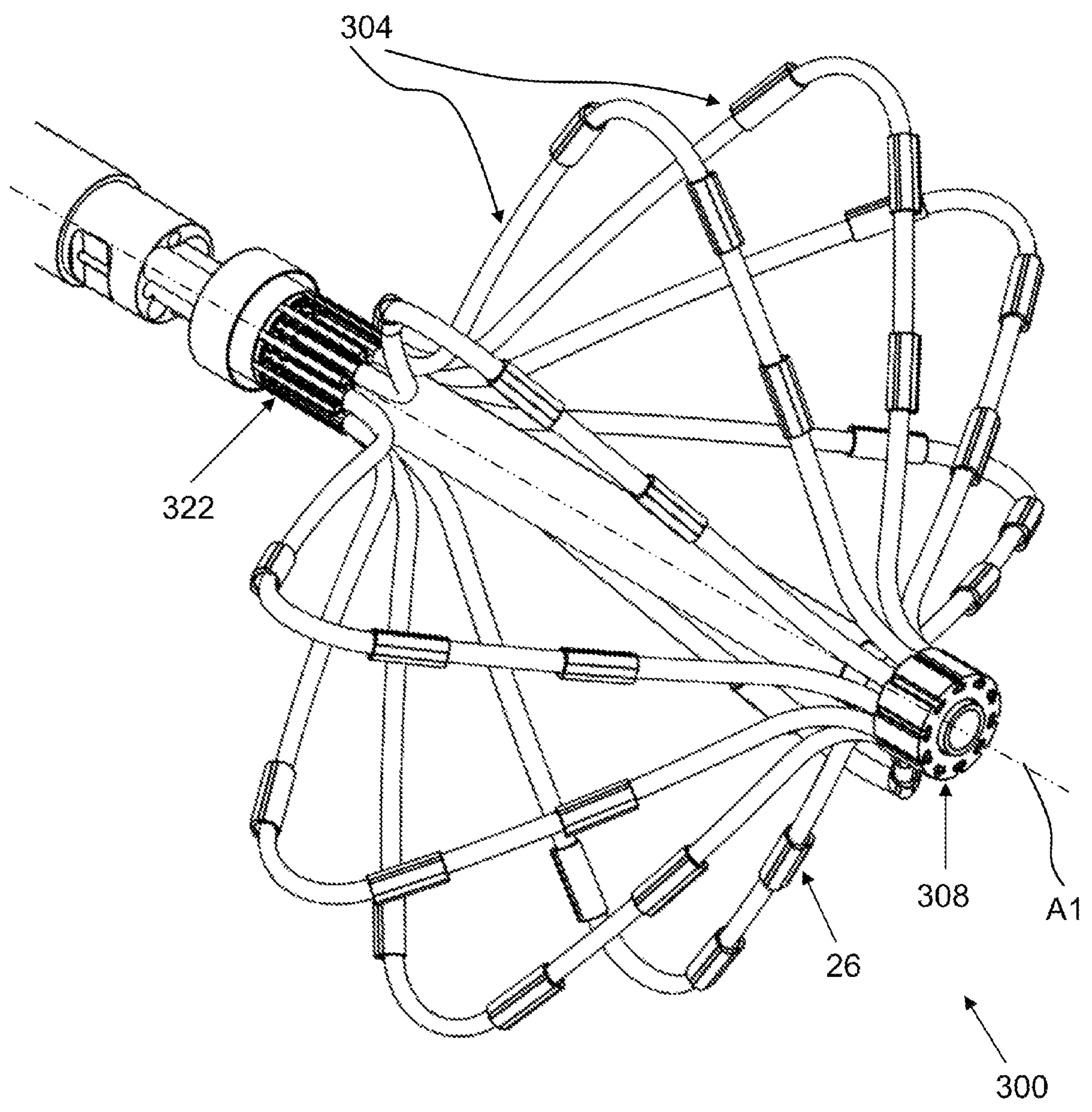
FIG. 11 is a schematic pictorial illustration showing a perspective view of the third end effector, similar to FIG. 10, with the elongated shaft, annulus, and coil removed for clarity, in accordance with the disclosed technology.
Figure 12:
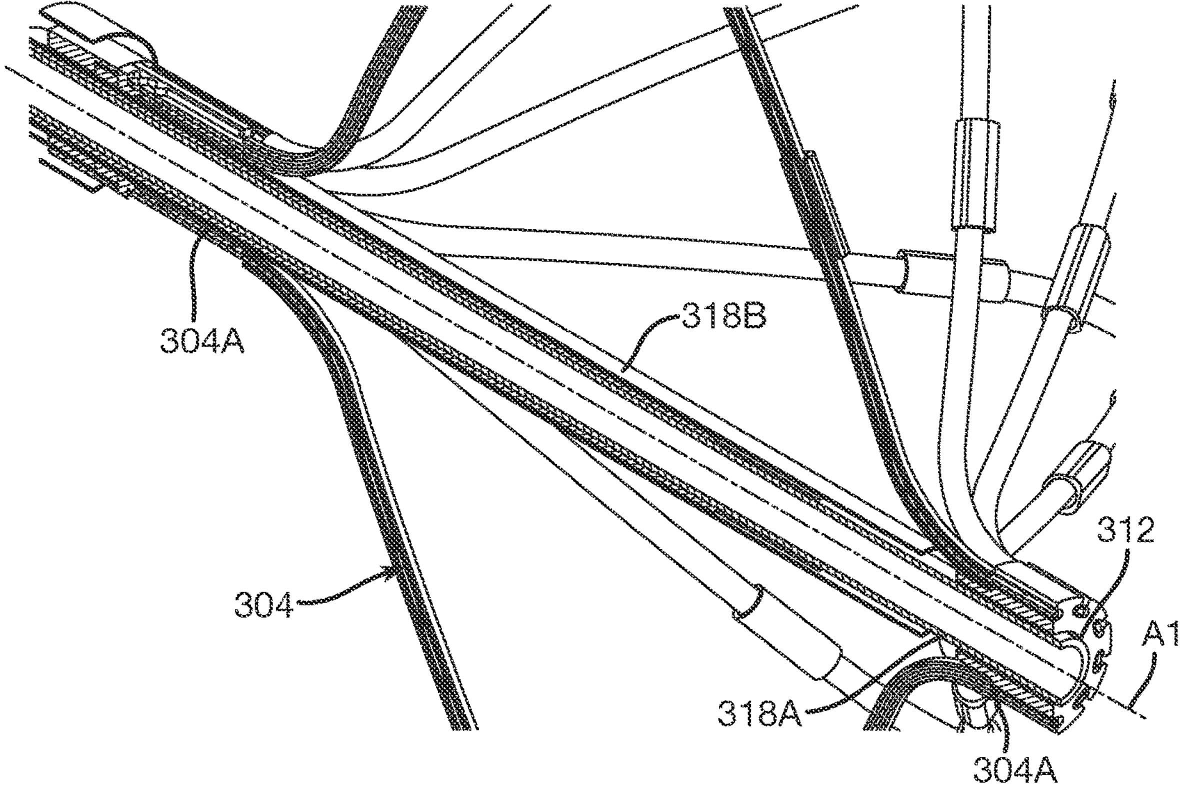
FIG. 12 is a schematic pictorial illustration showing a cross-sectional detail view of the third end effector shown in FIG. 11, cut relative to a vertical plane that intersects the longitudinal axis, in accordance with the disclosed technology.

FIG. 10 is a schematic pictorial illustration showing a perspective view of a third end effector 300. FIG. 11 is a schematic pictorial illustration showing a perspective view of the third end effector 300, similar to FIG. 10, with the elongated shaft 302, annulus 314, and coil 316 removed for clarity. FIG. 12 is a schematic pictorial illustration showing a cross-sectional detail view of the third end effector 200 shown in FIG. 11, cut relative to a vertical plane that intersects the longitudinal axis A1. Details specific to the third end effector 300 that contrast with the first end effector 100 and second end effector 200 are focused on in the following description. It will be appreciated that many of the features discussed with the previously discussed end effectors 100, 200 can be appropriately incorporated in the third end effector 300, and vice versa. By way of example, the third end effector 300 can have a similarly or identically designed elongated shaft 302, spines 304 with distal 304A and proximal 304B ends, distal hub 308, distal hub lumen 312, annulus 314, coil 316, and proximal sleeve 320. Making reference to FIG. 12, the actuator member 318 of the third end effector 300 includes an actuator rod 318 as well as an irrigation tube 318 which, while configured differently function in a similar manner as discussed above.

Figure 13:
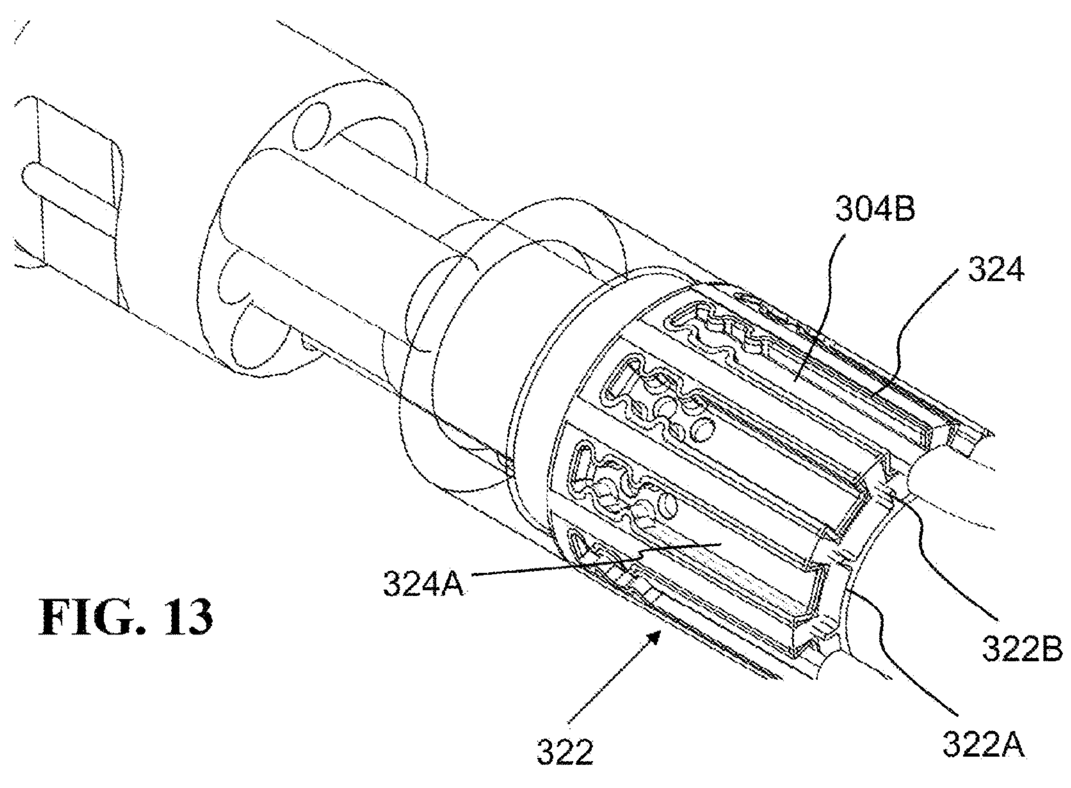
FIG. 13 is a schematic pictorial illustration showing a perspective detail view of the proximal end of the third end effector, with the sleeve and some spines removed for clarity, in accordance with the disclosed technology.
Figure 14:
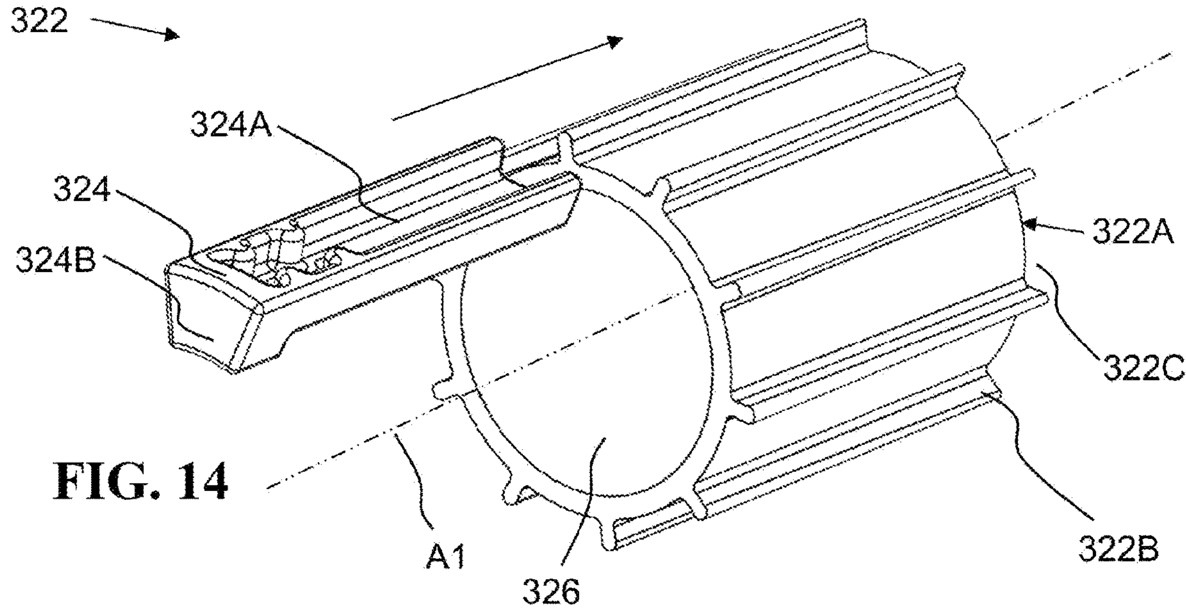
FIG. 14 is a schematic pictorial illustration showing an exploded detail view of the proximal hub of the third end effector, in accordance with the disclosed technology.
Figure 15:
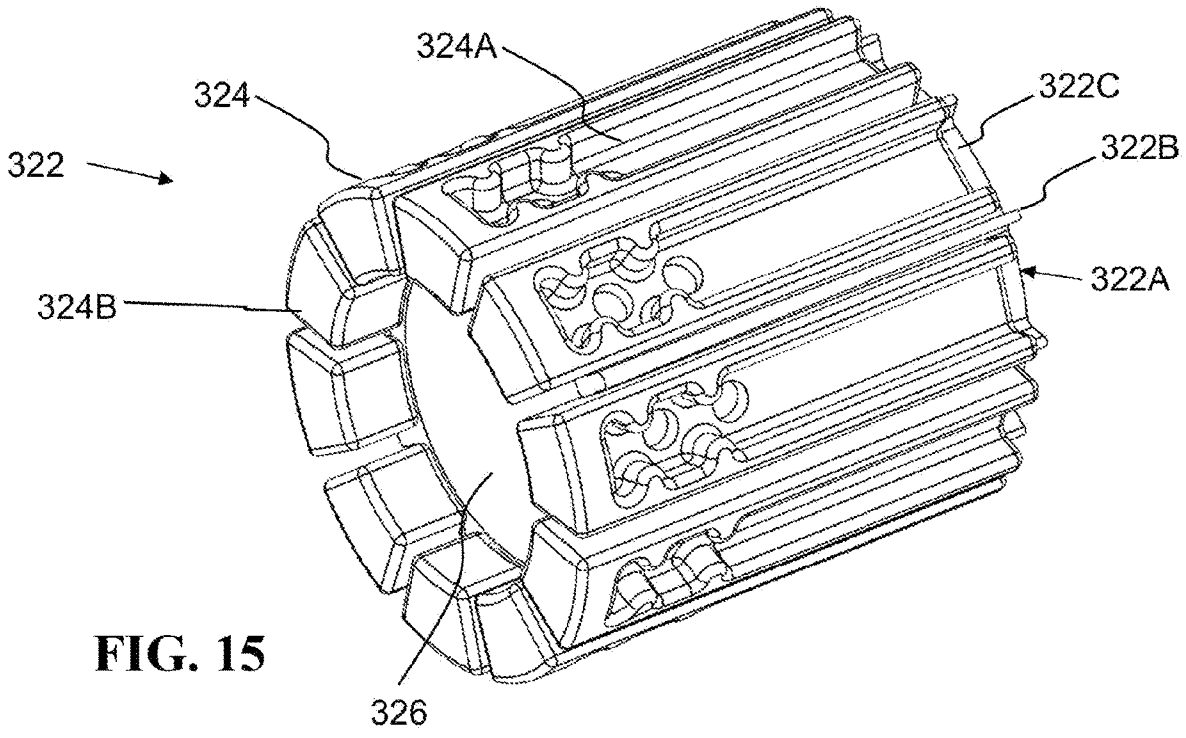
FIG. 15 is a schematic pictorial illustration showing a detail perspective view of the proximal hub of the third end effector, in accordance with the disclosed technology.
Figure 16:
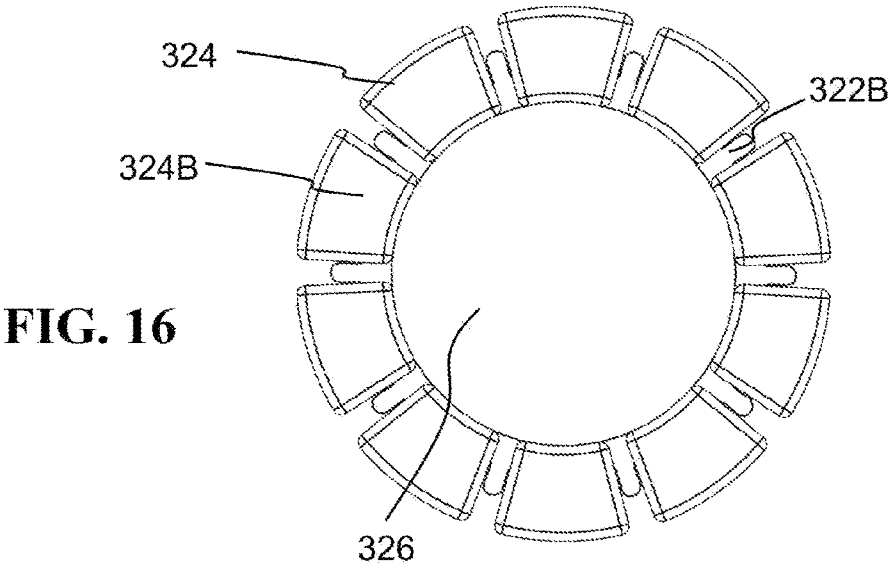
FIG. 16 is a schematic pictorial illustration showing a detail elevation view of the proximal hub of the third end effector, in accordance with the disclosed technology.

FIG. 13 is a schematic pictorial illustration showing a perspective detail view of the proximal end of the third end effector 300, with the sleeve 320 and some spines 304 removed for clarity. FIG. 14 is a schematic pictorial illustration showing an exploded detail view of the proximal hub 322 of the third end effector 300. FIG. 15 is a schematic pictorial illustration showing a detail perspective view of the proximal hub 322 of the third end effector 300. FIG. 16 is a schematic pictorial illustration showing a detail elevation view of the proximal hub 322 of the third end effector 300.

Referring now to FIGS. 13-16, the proximal hub 322, also referred to herein as the connecting hub, to which proximal ends 304B of the spines 304 are connected is formed from multiple components. The proximal hub 322 can be made from nitinol or any other appropriate bio-compatible material. Like the other described hubs, this proximal hub 322 includes a cylindrical body 322A that defines a proximal hub lumen 326 that directly or indirectly connects with the irrigation tube 318B. The cylindrical body 322A extends from a first terminal end (i.e., left-most end of the proximal hub 322 along the longitudinal axis A1, relative to FIG. 11) to a second terminal end (i.e., right-most end of the proximal hub 322 along the longitudinal axis A1, relative to FIG. 11) opposite the first terminal end. The cylindrical body 322A has fins 322B radially disposed about thereabout such that they protrude from the outer circumferential surface of the cylindrical body 322A. A receiving channel 322C is defined between adjacent fins 322B, which functions in a manner discussed in greater detail below.

Like the previously described examples, a plurality of recesses 324A are also provided that are radially disposed about the outer circumferential surface of the cylindrical body 322A and extend parallel to the longitudinal axis A1. However, in this example, the recesses 324A are formed in spine couplers 324, which are partially cuboid in form and have arcuate upper and lower surfaces as well as tapered side surfaces (see FIG. 16 for reference). On a proximal side thereof, the spine couplers 324 include a stop 324B protruding towards the longitudinal axis that engages the first terminal end of the cylindrical body 322A (FIG. 15) when engaged therewith (e.g., the spine couplers 324 can be slid onto the cylindrical body 322A in a direction denoted by the arrow in FIG. 14). As a result, the spine couplers 324 are partially offset from the cylindrical body 322A along the longitudinal axis A1 such that the stop 324B overhangs the cylindrical body 322A.

The stop 324B maintains the spine coupler 324 in position relative to the cylindrical body 322A and prevents the spine 304 from pulling the coupler 324 beyond the cylindrical body 322A. In other words, the stops 324B prevent longitudinal translation, in at least one direction, of the spine coupler 324 relative to the cylindrical body 322A. As seen particularly in FIGS. 15 and 16, the spine couplers 322C sit within the receiving channels 322C and are laterally constrained by the fins 322B.

Moreover, the recesses 324A formed in the upper surface of the spine coupler 324 are shaped to conform to the shape of the proximal ends 304B of the spines 304 (FIG. 13). Accordingly, to mate the recesses 324A and the proximal ends 304B, each proximal end 304B is slid into a respective recess 324A in a direction perpendicular to the longitudinal axis A1. The recesses 324A, due to the offset between the spine couplers 324 and the cylindrical body 322A, have an open end that terminates proximal (but not flush with) the second terminal end of the cylindrical body 322A (e.g., see the right side of FIG. 15). As can also be seen in FIG. 15, an end of the recess 324A opposite the open end is closed as it conforms to the shape of the distal tip of spines 304 it receives.

Figure 17:
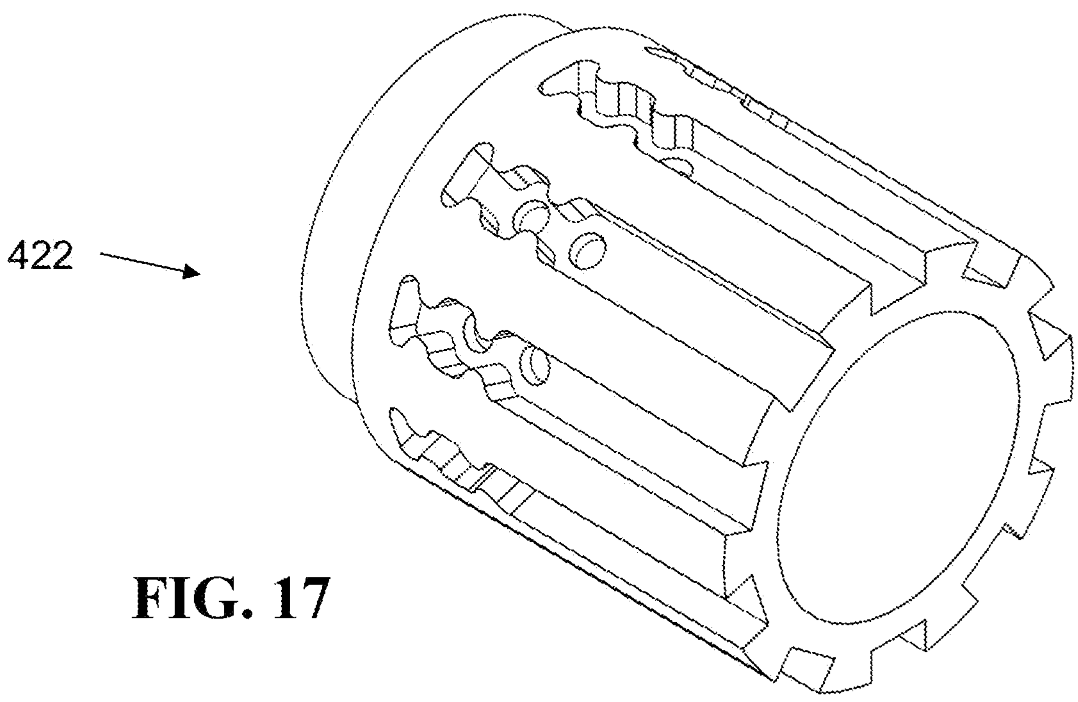
FIG. 17 is a schematic pictorial illustration showing a detail perspective view of yet another connecting hub, in accordance with the disclosed technology.

FIG. 17 is a schematic pictorial illustration showing a detail perspective view of yet another connecting hub 422. It is similar in structure to the afore-described proximal hub 322, but formed as a monolithic hub rather than separate components.

The disclosed technology described herein can be further understood according to the following clauses:

Clause 1. An end effector for a medical device, the end effector comprising: a plurality of spines extending along a longitudinal axis and configured to move between an expanded configuration and a collapsed configuration, each spine comprising a proximal end and a distal end; a plurality of electrodes connected to each spine; a connecting hub defining a hub lumen and comprising a first terminal end, a second terminal end, and a plurality of recesses that are radially disposed about an outer circumferential surface of the connecting hub and extend parallel to the longitudinal axis, each recess being open along the longitudinal axis at or proximal the first terminal end, each recess mating with one of the proximal end and the distal end of a respective spine of plurality of spines to prevent relative movement between the connecting hub and the spine; and an actuator member connected to the connecting hub and the plurality of spines so that translation of actuator member along the longitudinal axis moves the spines from the expanded to the collapsed configuration.

Clause 2. The end effector of clause 1, the one of the proximal end and the distal end sliding into the respective recess in a direction parallel to the longitudinal axis when the respective recess receives the one of the proximal end and the distal end.

Clause 3. The end effector of clause 1, the one of the proximal end and the distal end sliding into the respective recess in a direction perpendicular to the longitudinal axis when the recess receives the one of the proximal end and the distal end.

Clause 4. The end effector of any one of clauses 1-3, further comprising a connector tube extending parallel to the longitudinal axis and through the hub lumen from the proximal end of the plurality of spines to the distal end of the plurality of spines, the connector tube defining a connector tube lumen.

Clause 5. The end effector of clause 4, the connector tube defining a plurality of irrigation holes.

Clause 6. The end effector of clause 1, further comprising: an irrigation tube extending along the longitudinal axis, the actuator member comprising a puller wire extending through the irrigation tube and connected to the distal end of the plurality of the spines, the puller wire being configured to move the plurality of spines between the expanded configuration and the collapsed configuration.

Clause 7. The end effector of clause 1, further comprising: an irrigation tube extending along the longitudinal axis, the actuator member comprising an actuator rod extending through the irrigation tube and connected to the distal end of the plurality of the spines, the actuator rod being configured to move the plurality of spines between the expanded configuration and the collapsed configuration.

Clause 8. The end effector of clause 7, the actuator rod comprising a reference or return electrode.

Clause 9. The end effector of any one of clauses 7-8, the actuator rod defining an actuator rod lumen configured for a guidewire or a mapping catheter to pass therethrough.

Clause 10. The end effector of any one of clauses 6-9, the irrigation tube comprising pores for permitting saline to be distributed around each of the plurality of electrodes.

Clause 11. The end effector of any one of clauses 1-10, further comprising a proximal tubular housing that mates with the connecting hub along the longitudinal axis.

Clause 12. The end effector of clause 11, the proximal tubular housing extending through the hub lumen.

Clause 13. The end effector of any one of clauses 11-12, the connecting hub defining a plurality of hub grooves, and the proximal tubular housing comprising a plurality of housing grooves that align with the plurality of hub grooves along the longitudinal axis.

Clause 14. The end effector of clause 13, further comprising a plurality of electrical tubes that are each respectively received in the aligned plurality of housing grooves and plurality of hub grooves.

Clause 15. The end effector of any one of clauses 1-14, the plurality of electrodes comprising three electrodes connected to each spine, each three electrodes on respective spines laterally aligning with one another, the plurality of electrodes having a total tissue-contacting surface area sufficient to deliver 2000V of pulsed field ablation (PFA) pulses.

Clause 16. The end effector of any one of clauses 1-14, each spine having a midpoint, and the plurality of electrodes comprising four electrodes connected to each spine, with a first two of the four electrodes on a first side of the midpoint of each spine and a second two of the four electrodes on a second side of the midpoint of each spine.

Clause 17. The end effector of any one of clauses 1-16, further comprising a magnetic location sensor connected to the distal end of the plurality of spines.

Clause 18. A connecting hub for use with an end effector of a medical device, the connecting hub comprising: a first terminal end; a second terminal end opposite the first terminal end; a cylindrical body defining a hub lumen and extending along a longitudinal axis from the first terminal end to the second terminal end; and a plurality of recesses that are radially disposed about an outer circumferential surface of the cylindrical body and extend parallel to the longitudinal axis, each recess being open along the longitudinal axis at or proximal the first terminal end, and each recess being configured to mate with a proximal end or a distal end of a spine of the end effector.

Clause 19. The connecting hub of clause 18, each recess being defined in the outer circumferential surface of the cylindrical body.

Clause 20. The connecting hub of any one of clauses 18-19, each recess extending an entire length of the cylindrical body.

Clause 21. The connecting hub of any one of clauses 18-20, adjacent recesses defining a T-shaped formation therebetween, each recess spacing adjacent T-shaped formations.

Clause 22. The connecting hub of clause 21, opposing upper lateral sides of each T-shaped formation each defining a groove, with adjacent grooves of adjacent T-shaped formations forming a groove pair being configured to cooperatively receive an electrical tube.

Clause 23. The connecting hub of clause 22, each groove pair being disposed above the respective recess that spaces the respective adjacent T-shaped formations.

Clause 24. The connecting hub of any one of clauses 18-23, the connecting hub being monolithic.

Clause 25. The connecting hub of clause 18, further comprising a plurality of spine couplers that each engage the outer circumferential surface of the cylindrical body, the plurality of spine couplers comprising the plurality of recesses.

Clause 26. The connecting hub of clause 25, each spine coupler comprising a stop protruding towards the longitudinal axis, the stop preventing longitudinal translation in a first direction of the spine coupler relative to the cylindrical body.

Clause 27. The connecting hub of any one of clauses 25-26, each spine coupler being partially offset from the cylindrical body along the longitudinal axis such that each spine coupler overhangs the cylindrical body.

Clause 28. The connecting hub of any one of clauses 25-27, the cylindrical body comprising a plurality of fins that are radially disposed about the outer circumferential surface of the cylindrical body, adjacent fins receiving a respective spine coupler therebetween.

Clause 29. The connecting hub of any one of clauses 18-28, the plurality of recesses being shaped to correspond to a shape of the proximal end or the distal end of the spine of the end effector.

The examples described above are cited by way of example, and the disclosed technology is not limited by what has been particularly shown and described hereinabove. Rather, the scope of the disclosed technology includes both combinations and sub combinations of the various features described hereinabove, as well as variations and modifications thereof which would occur to persons skilled in the art upon reading the foregoing description and which are not disclosed in the prior art.

What is claimed is:

1. An end effector for a medical device, the end effector comprising:

a plurality of spines extending along a longitudinal axis and configured to move between an expanded configuration and a collapsed configuration, each spine comprising a proximal end and a distal end;

a plurality of electrodes connected to each spine;

a connecting hub defining a hub lumen and comprising a first terminal end, a second terminal end, and a plurality of recesses that are radially disposed about an outer circumferential surface of the connecting hub and extend parallel to the longitudinal axis, each recess of the plurality of recesses being open along the longitudinal axis at or proximal the first terminal end, each recess of the plurality of recesses mating with one of the proximal end and the distal end of a respective spine of plurality of spines to prevent relative movement between the connecting hub and the spine, adjacent recesses of the plurality of recesses defining a T-shaped formation therebetween, each recess of the plurality of recesses spacing adjacent T-shaped formations, opposing upper lateral sides of each T-shaped formation each defining a groove, with adjacent grooves of adjacent T-shaped formations forming a groove pair, each groove pair being disposed above the respective recess of the plurality of recesses that spaces the respective adjacent T-shaped formations;

a respective electrical tube cooperatively received in each groove pair radially aligned with a respective end of a respective spine of the plurality of spines mated in a respective recess of the plurality of recesses; and an actuator member connected to the connecting hub and the plurality of spines so that translation of actuator member along the longitudinal axis moves the spines from the expanded configuration to the collapsed configuration.

2. The end effector of claim 1, the one of the proximal end and the distal end configured to slide into the respective recess in a direction parallel to the longitudinal axis when the respective recess receives the one of the proximal end and the distal end.

3. The end effector of claim 1, the one of the proximal end and the distal end configured to slide into the respective recess in a direction perpendicular to the longitudinal axis when the respective recess receives the one of the proximal end and the distal end.

4. The end effector of claim 1, further comprising a connector tube extending parallel to the longitudinal axis and through the hub lumen from the proximal end of the plurality of spines to the distal end of the plurality of spines, the connector tube defining a connector tube lumen.

5. The end effector of claim 1, further comprising:

an irrigation tube extending along the longitudinal axis, the actuator member comprising a puller wire extending through the irrigation tube and connected to the distal end of the plurality of the spines, the puller wire being configured to move the plurality of spines between the expanded configuration and the collapsed configuration.

6. The end effector of claim 1, further comprising:

an irrigation tube extending along the longitudinal axis, the actuator member comprising an actuator rod extending through the irrigation tube and connected to the distal end of the plurality of the spines, the actuator rod being configured to move the plurality of spines between the expanded configuration and the collapsed configuration.

7. The end effector of claim 6, the actuator rod defining an actuator rod lumen configured for a guidewire or a mapping catheter to pass therethrough.

8. The end effector of claim 1, further comprising a proximal tubular housing that mates with the connecting hub along the longitudinal axis.

9. The end effector of claim 8, the proximal tubular housing extending through the hub lumen.

10. The end effector of claim 8, the connecting hub defining a plurality of hub grooves, and the proximal tubular housing comprising a plurality of housing grooves that align with the plurality of hub grooves along the longitudinal axis.

11. A connecting hub for use with an end effector of a medical device, the connecting hub comprising:

a first terminal end;

a second terminal end opposite the first terminal end;

a cylindrical body defining a hub lumen and extending along a longitudinal axis from the first terminal end to the second terminal end; and a plurality of recesses that are radially disposed about an outer circumferential surface of the cylindrical body and extend parallel to the longitudinal axis, each recess of the plurality of recesses being open along the longitudinal axis at or proximal the first terminal end, and each recess of the plurality of recesses being configured to mate with a proximal end or a distal end of a spine of the end effector; and a plurality of spine couplers that each engage the outer circumferential surface of the cylindrical body, the plurality of spine couplers comprising the plurality of recesses, each spine coupler comprising a stop protruding towards the longitudinal axis, the stop preventing longitudinal translation in a first direction of the spine coupler relative to the cylindrical body, each spine coupler being partially offset from the cylindrical body along the longitudinal axis such that each stop overhangs the cylindrical body.

12. The connecting hub of claim 11, the cylindrical body comprising a plurality of fins that are radially disposed about the outer circumferential surface of the cylindrical body, adjacent fins receiving a respective spine coupler therebetween.

13. The connecting hub of claim 11, the plurality of recesses being shaped to correspond to a shape of the proximal end or the distal end of the spine of the end effector.

* * * * *